(12) United States Patent
Eniola-Adefeso et al.

(10) Patent No.: US 12,296,048 B2
(45) Date of Patent: *May 13, 2025

(54) POLYMER PARTICLES FOR NEUTROPHIL INJURY

(71) Applicant: THE REGENTS OF THE UNIVERSITY OF MICHIGAN, Ann Arbor, MI (US)

(72) Inventors: Omolola Eniola-Adefeso, Ann Arbor, MI (US); William Kelley, Ann Arbor, MI (US); Theodore Standiford, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/519,530

(22) Filed: Nov. 27, 2023

(65) Prior Publication Data
US 2024/0197638 A1 Jun. 20, 2024

Related U.S. Application Data

(60) Continuation of application No. 17/481,525, filed on Sep. 22, 2021, now Pat. No. 11,826,469, which is a
(Continued)

(51) Int. Cl.
*A61K 9/19* (2006.01)
*A61K 9/00* (2006.01)
(Continued)

(52) U.S. Cl.
CPC .......... *A61K 9/1647* (2013.01); *A61K 9/0019* (2013.01); *A61K 9/1682* (2013.01);
(Continued)

(58) Field of Classification Search
CPC .. A61K 9/1647; A61K 9/0019; A61K 9/1682; A61K 9/19; A61K 31/616;
(Continued)

(56) References Cited

U.S. PATENT DOCUMENTS 4,522,811 A   6/1985  Eppstein et al.
11,376,221 B2 *  7/2022  Eniola-Adefeso ..... A61K 31/74
(Continued)

FOREIGN PATENT DOCUMENTS

| JP | 2003-511550 | 3/2003 |
| WO | WO 2001/028492 | 4/2000 |
| WO | WO 2021/007113 | 1/2021 |

OTHER PUBLICATIONS

Abdulnour et al. (Am J Respir Crit Care Med vol. 197, Iss 12, pp. 1575-1585, Jun. 15, 2018) (Year: 2018).*
(Continued)

*Primary Examiner* — Ernst V Arnold
(74) *Attorney, Agent, or Firm* — Casimir Jones, S.C.; Kirk J. Hogan

(57) ABSTRACT

Provided herein are methods of treatment, compositions, systems and kits using polymer particles as restraints of neutrophil function. Such methods include, but are not limited to, methods of preventing, treating, and/or ameliorating inflammatory diseases, infections, autoimmune diseases, malignant diseases, and other diseases or conditions in which neutrophils may be implicated. In some embodiments, polymer particles are useful for diagnosing neutrophil related diseases or conditions.

19 Claims, 31 Drawing Sheets

Related U.S. Application Data division of application No. 16/920,238, filed on Jul. 2, 2020, now Pat. No. 11,376,221.

(60) Provisional application No. 62/870,879, filed on Jul. 5, 2019.

(51) Int. Cl.
 *A61K 9/16* (2006.01)
 *A61M 25/01* (2006.01)
 *A61M 25/09* (2006.01)

(52) U.S. Cl.
 CPC ............... *A61K 9/19* (2013.01); *A61M 25/01* (2013.01); *A61M 2025/091* (2013.01)

(58) Field of Classification Search
 CPC ............... A61K 9/5138; A61M 25/01; A61M 2025/091; A61P 9/00; A61P 19/02; A61P 7/00
 See application file for complete search history.

(56) References Cited

U.S. PATENT DOCUMENTS

| | | | |
|---|---|---|---|
| 11,826,469 B2* | 11/2023 | Eniola-Adefeso | .... A61M 25/01 |
| 2012/0121622 A1 | 5/2012 | Van Nest et al. | |
| 2014/0271864 A1* | 9/2014 | Uhrich | ................... A61K 45/06 424/78.37 |
| 2016/0331774 A1 | 11/2016 | Rubin-Bejerano et al. | |
| 2021/0000745 A1 | 1/2021 | Eniola-Adefeso et al. | |

OTHER PUBLICATIONS

Abdulnour et al., Early Intravascular Events Are Associated with Development of Acute Respiratory Distress Syndrome. A Substudy of the LIPS-A Clinical Trial. Am J Respir Crit Care Med. Jun. 15, 2018;197(12):1575-1585.

Bharara et al., Intravenous Vitamin C Administered as Adjunctive Therapy for Recurrent Acute Respiratory Distress Syndrome. Case Rep Crit Care , articles ID 8560871; 2016, 4 pages.

Brannon et al., (2022). Polysalicylic Acid Polymer Microparticle Decoys Therapeutically Treat Acute Respiratory Distress Syndrome. Advanced healthcare materials, 11(7), e2101534.

Bryers, J.D., et al., Biodegradation of poly(anhydride-esters) into non-steroidal anti-inflammatory drugs and their effect on Pseudomonas aeruginosa biofilms in vitro and on the foreign-body response in vivo. Biomaterials, 2006. 27(29): p. 5039-48.

Deng, J.C., et al., Sepsis-induced suppression of lung innate immunity is mediated by IRAK-M. J Clin Invest, 2006. 116(9): p. 2532-42.

Deronde et al., Storage Stability Study of Salicylate-based Poly(anhydride-esters) Polymer Degradation and Stability, 2010. 95(9): p. 1778-1782.

Kendrew et al. (eds.), The Encyclopedia of Molecular Biology, published by Blackwell Science Ltd., 1994 TOC.

Lewin, *Genes V*, published by Oxford University Press, 1994 TOC.

Matthay et al., Acute respiratory distress syndrome. Nat Rev Dis Primers. 2019, 14;5(1):18.

Prudencio et al., Effect of Linker Structure on Salicylic Acid-Derived Poly(anhydride-esters). Macromolecules, 2005. 38(16): p. 6895-6901.

Meyers, Molecular Biology and Biotechnology: a Comprehensive Desk Reference, published by VCH Publishers, Inc., 1995.

Ouimet et al., (2012). Tunable drug release profiles from salicylate-based poly(anhydride-ester) matrices using small molecule admixtures. Journal of bioactive and compatible polymers, 27(6), 540-549.

Reynolds, et al., Non-steroidal anti-inflammatory drug (NSAID)-derived poly(anhydride-esters) in bone and periodontal regeneration. Current Drug Delivery, 2007. 4(3): p. 233-239.

Rosario-Melendez et al., Formulation of salicylate-based poly(anhydride-ester) microspheres for short- and long-term salicylic acid delivery. Polymer Bulletin 2013. 70(1): p. 343-351.

Schmeltzer et al., Synthesis and cytotoxicity of salicylate-based poly(anhydride esters). Biomacromolecules. Jan.-Feb. 2005;6(1):359-367.

Whitaker-Brothers et al., Investigation into the erosion mechanism of salicylate-based poly(anhydride-esters). J Biomed Mater Res A. Mar. 1, 2006;76(3):470-479.

Extended European Search Report issued for corresponding EP Appl. No. 20836323.4; mailed Jun. 5, 2023, 10 pages.

International Search Reported issued in corresponding International Application No. PCT/US2020/040754, mailed Sep. 30, 2020, 11 pages.

* cited by examiner

A

B

Mouse Model: BALB/c

Untreated Monocytes vs Neutrophils

LPS Monocytes vs Neutrophils

Lung injury by LPS

LPS + P Monocytes vs Neutrophils

Initial Studies Injecting at 6 hours

P. Aeruginosa Lung Infection Model

Survival

POLYMER PARTICLES FOR NEUTROPHIL INJURY

CROSS-REFERENCE TO RELATED APPLICATIONS

The present Application is a continuation of U.S. patent application Ser. No. 17/481,525, filed Sep. 22, 2021, now U.S. Pat. No. 11,826,469, which is a divisional of U.S. patent application Ser. No. 16/920,238, filed Jul. 2, 2020, now U.S. Pat. No. 11,376,221, which claims priority to U.S. Provisional Application Ser. No. 62/870,879 filed Jul. 5, 2019, the each of which is incorporated by reference herein.

FIELD OF THE INVENTION

Provided herein are methods of treatment, compositions, systems and kits using polymer particles as restraints of neutrophil function. Such methods include, but are not limited to, methods of preventing, treating, and/or ameliorating inflammatory diseases, infections, autoimmune diseases, malignant diseases, and other diseases or conditions in which neutrophils may be implicated. In some embodiments, polymer particles are useful for diagnosing neutrophil related diseases or conditions.

BACKGROUND OF THE INVENTION

Neutrophil-based medical conditions comprise a diversity of medical conditions including vascular thrombosis, inflammatory arthritides, systemic lupus erythematosus (SLE), atherosclerosis, sepsis and acute lung injury. For example, acute lung injury (ALI) is a rapidly progressing inflammatory disease characterized by disruption of the lung endothelial and epithelial barriers leading to accumulation of fluids in the alveolar airspace. Blood-gas barrier damage impairs gas exchange and reduces lung function. ALI together with acute respiratory distress syndrome (ARDS), a more severe form of ALI, affects 200,000 patients per year in the US, with a mortality rate of ~40% with a mortality rate of ~50-60% up to 6 months after hospital discharge. No pharmacological intervention is effective in reducing mortality in ALI/ARDS. For example, nitric oxide to decrease ARDS-related pulmonary hypertension, exogenous surfactants, intravenous prostaglandin E1, and glucocorticoids have shown no benefit in resolving ALI/ARDS. The primary treatment for ARDS is supportive with use of a mechanical ventilator for blood oxygenation and $CO_2$ removal, thereby allowing the damaged lung to heal. However, further damage to the lung may occur with mechanical ventilation if not employed with care. Hence, management of ALI/ARDS is an unmet clinical need.

SUMMARY OF THE INVENTION

Provided herein are methods of treatment, compositions, systems and kits using polymer particles as restraints of neutrophil function. Such methods include, but are not limited to, methods of preventing, treating, and/or ameliorating inflammatory diseases, infections, autoimmune diseases, malignant diseases, and other diseases or conditions in which neutrophils may be implicated. In some embodiments, polymer particles are useful for diagnosing neutrophil related diseases or conditions.

In some embodiments, provided herein are methods of treating, ameliorating, or preventing recurrence of a neutrophil-mediated inflammatory condition in a patient comprising administering to the patient a therapeutically effective amount of a salicylate polyanhydride ester that hydrolyzes to salicylic acid (as used herein "Poly-A") particle and pharmaceutically acceptable carrier, and/or pharmaceutically acceptable formulation. In certain embodiments, the Poly-A particle is a vascular-targeted particle (VTP). In other embodiments, the Poly-A particle is a non-targeted particle (nTP). In particular embodiments, the neutrophil-mediated condition is one or more conditions selected from vascular thrombosis, inflammatory arthritis, systemic lupus erythematosus (SLE), atherosclerosis, sepsis, arthritis, acute lung injury (ALI) and acute respiratory distress syndrome (ARDS). In particular embodiments, the patient is a mammal. In other embodiments, the mammal is a human.

In some embodiments, the administering is intravascular administering. In certain embodiments, the administering is intravenous administering. In further embodiments, the administering is administering using a guided catheter guided by, for example, X-radiology imaging, ultrasound imaging, computerized axial tomography imaging, and/or magnetic resonance imaging.

In some embodiments, the Poly-A particle is a microparticle with a dimension, for sample, of 500 to 900 nm or greater. In other embodiments, the Poly-A particle is a nanoparticle with a dimension, for example, of less than 500 nm. In certain embodiments, the Poly-A particle is a sphere. In other embodiments, the microparticle is a microsphere. In particular embodiments, the sphere comprises a smooth surface. In further embodiments, the Poly-A particle comprises a diversity of Poly-A particles that differ in dimension, shape, and/or surface morphology.

In some embodiments, the present invention provides a kit comprising a pharmaceutical composition comprising a Poly-A particle, and, optionally, instructions for administering the pharmaceutical composition to a patient diagnosed with vascular thrombosis (for example, venous thromboembolism), inflammatory arthritis, systemic lupus erythematosus (SLE), atherosclerosis, infection (for example, viral infection), sepsis, acute lung injury arthritis (ALI) and acute respiratory distress syndrome (ARDS).

In some embodiments, the present invention provides a method of inhibiting signs of inflammation, comprising exposing to a sample comprising inflammatory cells a composition comprising a Poly-A particle, wherein said exposing results in inhibition of signs of inflammation. In certain embodiments, the sample is from a human. In particular embodiments, the human is diagnosed with vascular thrombosis, inflammatory arthritis, systemic lupus erythematosus (SLE), atherosclerosis, sepsis, acute lung injury arthritis (ALI) and acute respiratory distress syndrome (ARDS). In other embodiments, the sample is a sample selected from the group consisting of a blood sample, a serum sample, a plasma sample, a saliva sample, a urine sample, a synovial fluid sample, a cartilage sample, and a tissue sample.

In some embodiments, the present invention provides a pharmaceutical composition comprising at least one Poly-A particle. In certain embodiments, the Poly-A particle is a targeted Poly-A particle. In other embodiments, the targeted Poly-A particle is a Poly-A VTP. In further embodiments, the Poly-A particle is a nTP. In particular embodiments, the Poly-A particle is biocompatible and biodegradable. In a given embodiment, that Poly-A particle comprises a bioactive molecule.

In some embodiments, the present invention provides a pharmaceutical composition consisting of at least one Poly-A particle and at least one pharmaceutically acceptable carrier. In some embodiments, the present invention provides a pharmaceutical composition wherein at least one Poly-A particle is made by the method of one or more or all of the steps of: a) dissolving polyvinyl alcohol (PVA) with an average molecular weight of 20-70 kDA in water to generate a 1 wt % PVA solution of pH 6-7; b) dissolving Poly-A in dichloromethane (DCM); c) adding the solution comprising the Poly-A in the DCM to the PVA solution over at least one hour during mixing at >4000 rpm to generate an emulsion; d) centrifuging the emulsion; e) aspirating a centrifuged solution from a centrifuged pellet; f) resuspending the pellet in deionized water to generate suspended Poly-A particles; g) washing the suspended Poly-A particles; h) lyophilizing the washed Poly-A particles; and i) freezing the lyophilized Poly-A particles. In other embodiments, the Poly-A particle is modified to be a carrier of one or more hydrophobic bioactive compounds or drugs by adding the one or more hydrophobic bioactive compounds or drugs to the Poly-A polymer dissolved in said DCM. In further embodiments, the Poly-A particle is modified to be a carrier of one or more hydrophilic bioactive compounds or drugs by adding the one or more of the hydrophilic bioactive compounds or drugs to a water phase that is emulsified into the Poly-A polymer dissolved in said DCM, and emulsifying the drug-polymer emulsion in a solution of 1 wt % PVA in water.

In some embodiments, the present invention provides a pharmaceutical composition consisting of at least one PLGA particle and at least one pharmaceutically acceptable carrier. In some embodiments, the present invention provides a pharmaceutical composition wherein at least one PLGA particle is made by the method of one or more or all of the steps of: a) dissolving polyvinyl alcohol (PVA) with an average molecular weight of 20-70 kDA in water to generate a 0.5 wt % PVA solution of pH 5-6; b) dissolving PLGA (50:50 PLGA (molecular weight of, for example, 6.4 kDA in dichloromethane (DCM); c) adding the solution comprising the PLGA in the DCM to the PVA solution over at least one hour during mixing at >4000 rpm to generate an emulsion; d) centrifuging the emulsion to remove larger particles; e) centrifuging the supernatant to collect ~1.5 um particles; f) aspirating a centrifuged solution from a centrifuged pellet; g) resuspending the pellet in deionized water to generate suspended PLGA particles in a solution; h) flash freezing said solution; i) lyophilizing said PLGA particles; and j) freezing said lyophilized PLGA particles.

In some embodiments, the present invention provides a pharmaceutical composition wherein at least one Poly-A VTP particle is made by the method of one or more or all of the steps of: a) suspending Poly-A particles in 50 mM MES buffer; b) suspending the particles in Neutravidin solution in 50 mM MES; c) adding 1-ethyl-3-[3-(dimethylamino)propyl]carbodiimide hydrochloride (EDC) solution to the suspended particles; d) adding glycerine to the solution comprising the Poly-A particles; e) centrifuging the solution; f) resuspending the Poly-A particles in PBS; and g) incubating the solution comprising the Poly-A particles with biotinylated anti-ICAM-1 in PBS −/− with 2% BSA.

The foregoing and other objects, features, and advantages of the invention will become more apparent from the following detailed description, which proceeds with reference to the accompanying figures.

DEFINITIONS AND METHODS

Figure 1:
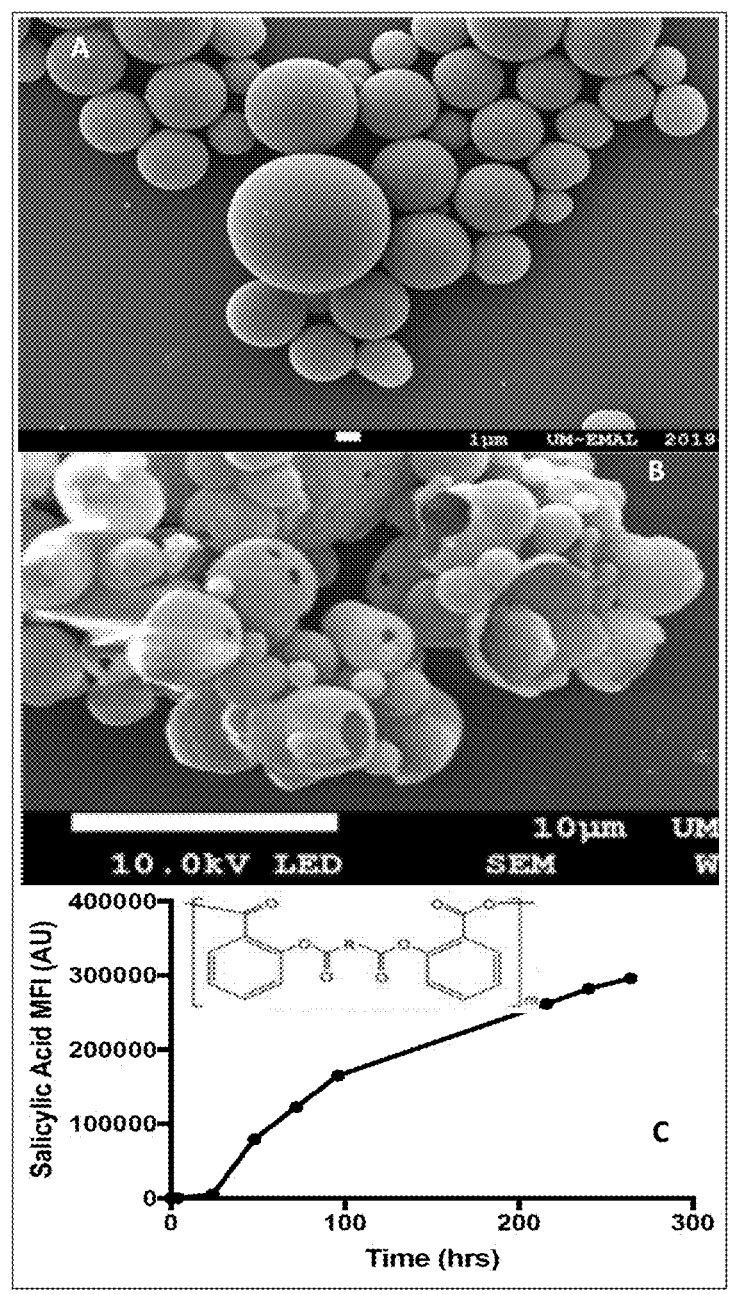
FIG. 1: Shows a scanning electron microscopy (SEM) image of Poly-A particles fabricated via emulsion solvent evaporation (ESE) method after (A) 0 and (B) 10 days of hydrolytic degradation in water. (C) shows release of salicylic (SA) from degrading Poly-A spheres measured by fluorescence intensity of SA in the media over time.

While the invention will be described in conjunction with certain representative embodiments, it will be understood that the invention is not limited to these illustrative examples. One skilled in the art will recognize many methods and materials similar or equivalent to those described herein may be used in the practice of the present invention. The present invention is in no way limited to the methods and materials described.

Unless defined otherwise, technical and scientific terms used herein have the meaning commonly understood by one of ordinary skill in the art to which this invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods, devices, and materials similar or equivalent to those described herein can be used in the practice of the invention, certain methods, devices, and materials are described herein. It is further to be understood that all base sizes or amino acid sizes, and all molecular weight or molecular mass values, given for nucleic acids or polypeptides are approximate, and are provided for description.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

As used in this disclosure, including the appended claims, the singular forms "a," "an," and "the" include plural references, unless the content clearly dictates otherwise, and are used interchangeably with "at least one" and "one or more." Thus, reference to "a Poly-A MP" includes mixtures of Poly-A MPs, and the like.

As used herein, the term "about" represents an insignificant modification or variation of the numerical value such that the basic function of the item to which the numerical value relates is unchanged.

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "inflammatory disease" refers to a disease or condition involving an inflammatory response. The inflammatory response may be acute and/or chronic. In some embodiments, chronic inflammation involves an increase neutrophil number and/or activity. Non-limiting exemplary inflammatory diseases that may be treated with Poly-A particles described herein include rheumatoid arthritis, juvenile idiopathic arthritis, systemic-onset juvenile idiopathic arthritis, osteoarthritis, sepsis, asthma, interstitial lung disease, inflammatory bowel disease, systemic sclerosis, intraocular inflammation, Grave's disease, endometriosis, systemic sclerosis, adult-onset Still disease, amyloid A amyloidosis, polymyalgia rheumatic, remitting seronegative symmetrical synovitis with pitting edema, Behcet's disease, uveitis, graft-versus-host diseases, venous thromboembolism, ALI/ARDS and TNFR-associated periodic syndrome.

As used herein, "infection" refers to a disease or condition caused by a pathogen, such as a bacteria, virus, fungus, etc. Non-limiting exemplary infections that may be treated with the Poly-A particles described herein include bacterial, viral, fungal, rickettsial, and parasitic infections. In some embodiments, the viral infection is a respiratory virus infection including, for example, influenza virus infection, corona virus infection (e.g. severe acute respiratory syndrome coronavirus 2 (SARS-COV2)), and respiratory syncytial viral infection.

As used herein, "autoimmune disease" refers to a disease or condition arising from an inappropriate immune response against the body's own components, such as tissues and other components. In some embodiments, neutrophil numbers and activity are elevated in autoimmune disease. Non-limiting exemplary autoimmune diseases that may be treated with the Poly-A particles described herein include systemic lupus erythromatosus, systemic sclerosis, polymyositis, vasculitis syndrome including giant cell arteritis, takayasu aeteritis, cryoglobulinemia, myeloperoxidase-antineutrophil cytoplasmic antibody-associated crescentic glomerulonephritis, rheumatoid vasculitis, Crohn's disease, relapsing polychondritis, acquired hemophilia A, and autoimmune hemolytic anemia.

As used herein, a "neutrophil mediated condition or disease" refers to a disease or condition in which at least some of the symptoms and/or progression of the disease or condition is caused neutrophil accumulation and/or activity. Non-limiting exemplary neutrophil mediated diseases or conditions include inflammatory diseases, malignant diseases (including cancer and cancer-related conditions), infections, and autoimmune diseases. Further non-limiting exemplary neutrophil mediated diseases include, but are not limited to, Castleman's disease, ankylosing spondylitis, coronary heart disease, cardiovascular disease in rheumatoid arthritis, pulmonary arterial hypertension, chronic obstructive pulmonary disease (COPD), atopic dermatitis, psoriasis, sciatica, venous thrombosis, type II diabetes, obesity, giant cell arteritis, acute graft-versus-host disease (GVHD), non-ST elevation myocardial infarction, anti-neutrophil cytoplasmic antibody (ANCA) associated vasculitis, neuromyelitis optica, chronic glomerulonephritis, and Takayasu arteritis.

As used herein, "modulate" means to alter, either by increasing or decreasing, the number and/or activity of a cell. The term "inhibit", as used herein, means to prevent or reduce cell number and/or activity. A used herein the cell that is modulated is a neutrophil.

As used herein, the term "bioactivity" indicates an effect on one or more cellular or extracellular process (e.g., via binding, signaling, etc.) which can impact physiological or pathophysiological processes.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" and/or "formulation" refers to a diluent, adjuvant, excipient, or vehicle with which the therapeutic is administered and includes, but is not limited to, such sterile liquids as water and oils.

A "pharmaceutically acceptable salt" or "salt" is a product of a disclosed compound that contains an ionic bond and is typically produced by reacting the disclosed compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising a Poly-A polymer particle in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, intra-articular, intra-ocular, and rectal administration.

As used herein, the term "therapeutically effective amount" generally means the amount necessary to ameliorate at least one symptom of a disorder or condition to be prevented, reduced, or treated as described herein. The phrase "therapeutically effective amount" as it relates to the Poly-A particle of the present disclosure means the Poly-A particle dosage that provides the specific pharmacological response for which the Poly-A particle is administered in a significant number of individuals in need of such treatment. It is emphasized that a therapeutically effective amount of a Poly-A particle that is administered to a particular individual in a particular instance will not always be effective in treating the conditions/diseases described herein, even though such dosage is deemed to be a therapeutically effective amount by those of skill in the art.

As used herein, the term "second agent" refers to a therapeutic agent other than a Poly-A particle in accordance with the present invention. In certain instances, the second agent is an anti-inflammatory agent.

As used herein, the term "sepsis" refers to the presence of the presence of harmful microorganisms in the blood.

The term "co-administration" refers to the administration of at least two agent(s) (e.g., a Poly-A particle) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "combination therapy" includes the administration of an anti-inflammatory agent (e.g., a Poly-A particle) and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule or injection having a fixed ratio of each therapeutic agent or in multiple, single capsules or injections for each of the therapeutic agents. Sequential or substantially simultaneous administration of each therapeutic agent can be affected by any appropriate route including, but not limited to, oral routes, intravenous routes, intramuscular routes, intra-articular routes, corneal routes, topical routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Ranges provided herein are understood to be shorthand for all of the values within the range. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

DETAILED DESCRIPTION

Provided herein are methods of treatment, compositions, systems and kits using polymer particles as restraints of neutrophil function. Such methods include, but are not limited to, methods of preventing, treating, and/or ameliorating inflammatory diseases, infections, autoimmune diseases, malignant diseases, and other diseases or conditions in which neutrophils may be implicated. In some embodiments, polymer particles are useful for diagnosing neutrophil related diseases or conditions.

ALI/ARDS

Numerous and complex pathologies lead to ALI/ARDS. Either a direct or an indirect injury initiates ALI/ARDS with no differences in the overall mortality. A direct pulmonary injury occurs with pathologies that start in the lungs, e.g., pneumonia, that induce activation of lung macrophages and are followed by damage to the lung epithelia. The cascade of inflammatory events in the lungs then triggers inflammation of the lung endothelium, and the recruitment of primary leukocytes from the blood into the lungs, thereby propagating the injury. An indirect injury arises from a pathology outside the lungs e.g., sepsis or trauma, in which the disease results in systemic inflammation that initiates rapid leukocyte migration into the lungs. Migration of leukocytes damages the lung endothelium and eventually the lung epithelia. Regardless of the primary cause of ALI, the outcome is a damaged alveolar epithelium, leading to the rapid infiltration of the alveoli by immune cells and protein-rich fluid causing compromised lung function.

Neutrophils in ALI/ARDS

The inflammatory cascade in ALI/ARDS triggers the capillary endothelium to express leukocyte adhesion molecules (LAMs) that facilitate the rapid migration of circulating blood neutrophils. LAMs including selectin, intracellular adhesion molecule (ICAM)-1 and vascular cell adhesion molecule (VCAM)-1 promote rapid migration of circulating white blood cells (WBCs) and leukocytes in the lung tissue. Neutrophils are the most abundant WBCs comprising 60%-70% of WBC counts, and are the most efficient first responders in acute inflammation. Accordingly, neutrophils are the primary cell type in bronchoalveolar lavage fluid (BALF) from ARDS patients, and disease severity correlates with the concentration of neutrophils in BALF samples. Neutrophils are the primary perpetrator of inflammation in ALI/ARDS causing damage in at least 2 ways. First, excess migration of neutrophils into the lungs contributes to destruction of the alveolar-capillary barrier that leads to edema in lungs. Second, neutrophils accumulate in the lung tissue and alveolar airspace, and release damaging pro-inflammatory and pro-apoptotic factors that impact resident cells and that give rise to further damage to the lungs. Halting the negative contribution of neutrophils provides an opportunity for targeted treatment of ALI/ARDS and other inflammatory conditions. Drugs that block or suppress expression of LAMs e.g., lisophylline and talactoferrin, have failed in clinical trials. CD11b/CD18 (Mac-1) integrin is important in *Escherichia* (*E.*) *coli* LPS and *Pseudomonas* (*P.*) *aeruginosa*-induced ALI, but blocking CD18 reduces neutrophil lung migration by only 60%.

In experiments conducted in the course of development of embodiments of the present invention, non-targeted and vascular-targeted nanoparticles and microparticles (VTPs) (e.g., particles with surfaces bound with an antibody or ligand that targets proteins expressed on the vascular wall including, for example, anti-E-selectin antibody, anti-ICAM-1 antibody, anti-VCAM-1 antibody, and the like, and other peptides and carbohydrates that bind selectins and LAMs) have been discovered to passively (i.e., without an active pharmaceutical ingredient (API)), and rapidly block neutrophil accumulation into inflamed tissue in ALI/ARDS, thereby halting their destructive role in ALI/ARDS. Polystyrene (PS) VTPs in human blood flow interact with and reduce vascular wall adhesion of neutrophils to a monolayer of activated endothelial cells (ECs) in vitro in a parallel plate flow chamber. Selectin-targeted, polystyrene (PS) VTPs provide nearly 100% reduction in neutrophil adhesion by physical coverage of the EC surface, thus blocking neutrophil attachment. At high particle concentrations, neutrophil adhesion is prevented both by physical coverage of the EC surface, and by free stream particle-cell interactions (~55% reduction in WBC adhesion with non-targeted, non-adhesive particles at 108 particles/ml of blood), demonstrating that PS-VTPs in human blood alter neutrophil-vascular wall adhesion, and providing a new opportunity for anti-inflammatory therapy in ALI wherein rapid intervention is desirable. In a lipopolysaccharide (LPS) mouse model of ALI, LPS administered to the lungs of healthy mice induces rapid recruitment of neutrophils into the lungs. When LPS-ALI mice are treated with 2 µm PS microparticles administered 1 hour after LPS instillation via tail vein injection at 30 mg/kg, the total lung lavage neutrophil count drops by 93% to $2.9 \times 10^6$ from the LPS-only mice. LPS-treated mice that received 500 nm PS-VTPs had a drop in total BALF neutrophil to $6.4 \times 10^5$, equaling a 98% decrease from the LPS-only mice. Both PS particle-treated groups were not statistically different from the untreated (no LPS) mice. Although both particle sizes induced the same level of neutrophil reduction in LPS-treated mice, microparticles more efficiently reduced lung neutrophil count compared to nanoparticles in view of 64 times more nanoparticles injected by number equivalent to dosing by mass. LPS instillation alone does not result in migration of monocytes or change in the absolute number of macrophages in the lungs with or without particle injection. Although the methods, compositions, kits and systems of the present invention are not restricted to a particular mechanism, polymer particles appear to achieve therapeutic benefit against unwanted neutrophil accumulation in the airspace in ALI/ARDS through physical interactions that reduce leukocyte adhesion to inflamed endothelium (e.g., collisions in blood flow that disrupt leukocyte adhesion, specific binding to LAMs expressed by the endothelium in inflamed tissue in competition with leukocytes for binding sites, particle phagocytosis/internalization that alters leukocyte phenotypes, and diversion of neutrophils from the lung and blood to the liver). These features stand apart from the use of polymer particles as a drug or bioactive compound carrier, i.e., VTC's, configured for delivery of a bioactive molecule (e.g. a protein or peptide antigen directed towards the cells of adaptive immunity), or a pharmacologic molecule. Thus, polymer particles that target neutrophils provide previously unknown therapies for neutrophil-mediated inflammatory and other conditions, including vascular thrombosis, inflammatory arthritides, systemic lupus erythematosus (SLE), atherosclerosis, sepsis and ALI/ARDS.

The present invention provides polymer particles formed from, for example, a biodegradable, biocompatible Poly-A polymer that block neutrophil migration. Non-toxic degradation product of the Poly-A polymer (i.e., salicylic acid) is itself anti-inflammatory, with the added benefit of Poly-A particles for treatment in ALI/ARDS e.g., Poly-A particles are targeted to block neutrophil migration into the lung airway in ALI/ARDS, and locally release salicylic acid to further treat lung injury. In this fashion, it is contemplated that local neutrophil adhesion at an inflammation site is halted, migration of neutrophils into lung tissue and the airspace is rapidly and efficiently prevented with minimal system impact, host protective responses are preserved, and biodegradation is rapid. Direct action of Poly-A particles on neutrophils in the blood vessels of the lungs and other tissues after intravascular injection, rather than indirect blocking adhesion or signaling molecules, ensures that Poly-A polymer particles function irrespective of the primary direct or indirect cause of ALI/ARDS, or other conditions in which neutrophils participate in the pathogenesis, such as vascular thrombosis, inflammatory arthritides, systemic lupus erythematosus (SLE), atherosclerosis, infection and sepsis.

Poly-A Microparticles

Figure 8:
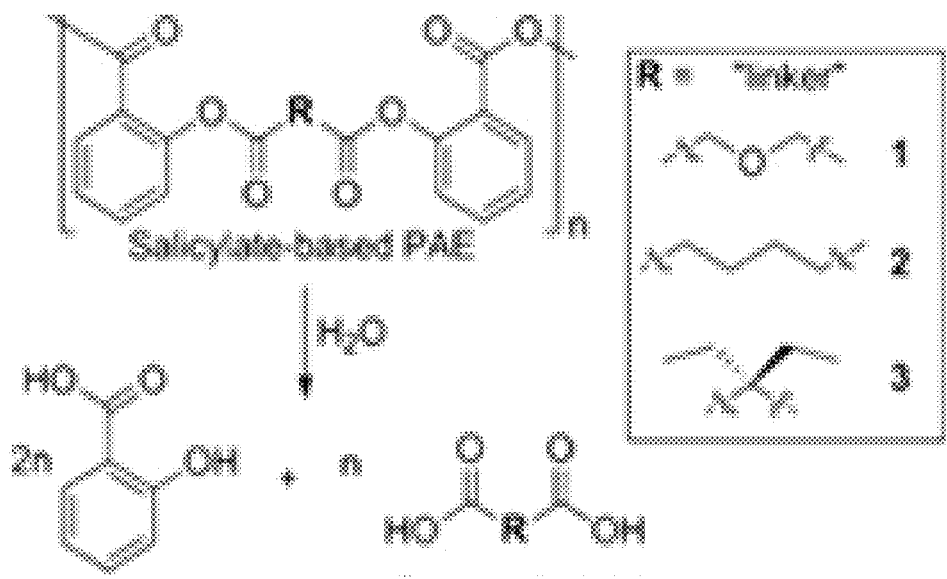
FIG. 8: Shows structures of polymers 1-3 of use in formulating salicylate-based Poly-A microspheres and their hydrolytic degradation of SA release.

FIG. 1c and FIG. 8 show structure of a Poly-A polymer wherein "R" corresponds to linkers that range from small molecular weight linear hydrocarbons to branched aliphatic hydrocarbons. The Poly-A polymer particle is biocompatible (Reynolds, M. A., A. Prudencio, M. E. Aichelmann-Reidy, K. Woodward, and K. E. Uhrich. Non-steroidal anti-inflammatory drug (NSAID)-derived poly(anhydride-esters) in bone and periodontal regeneration. Curr Drug Deliv, 2007. 4(3): p. 233-9, Bryers, J. D., R. A. Jarvis, J. Lebo, A. Prudencio, T. R. Kyriakides, and K. Uhrich. Biodegradation of poly(anhydride-esters) into non-steroidal anti-inflammatory drugs and their effect on *Pseudomonas aeruginosa* biofilms in vitro and on the foreign-body response in vivo. Biomaterials, 2006. 27(29): p. 5039-48) and stable under dry storage conditions Deronde, B. M., A. L. Carbone, and K. E. Uhrich, Storage Stability Study of Salicylate-based Poly (anhydride-esters). Polym Degrad Stab, 2010. 95(9): p. 1778-1782.) When placed in aqueous solutions, the polymer degrades to release salicylic acid (SA), which retains its anti-inflammatory properties. In some embodiments, emulsion solvent evaporation (ESE) techniques are used to fabricate degradable microspheres (FIG. 1A) from the Poly-A polymer having adipic acid as the linker, i.e., R=(CH$_2$)$_4$ and MW ~20 KDA. (FIG. 8) 20 mg of the Poly-A polymer (Mw=~20 kDa) is dissolved in 20 mL dichloromethane (oil phase) and the solution is emulsified into a solution of 1 wt % PVA in water (75 ml; aqueous phase). The oil phase is slowly injected via a syringe needle, and the emulsion is stirred continuously for up to 2 hrs, allowing for hardening of the oil droplets. The resultant Poly-A particles are washed twice via centrifugation and dried via lyophilization. Particles are stored at −40° ° C. until use. The generated Poly-A particles undergo hydrolytic degradation (FIG. 1C), and sustained release of salicylic acid (SA) (FIG. 1C).

In some embodiments, Poly-A particles of the present invention are spherical. In certain embodiments, the Poly-A particles range from 100 nm to 2 um in diameter. In particular embodiments, Poly-A spheres are fabricated with the polymer having the adipic acid linker (R=(CH$_2$)$_4$) and a molecular weight (Mw) of ~20 kDa via the oil-in-water ESE method as described previously. In other embodiments, the Poly-A particles are non-spherical, and/or irregular in shape and surface morphology including, for example, rods, ovals, stars, cones, cubes and the like. In further embodiments, the Poly-A particles in a single administration are uniform in size, shape and surface morphology. In still further embodiments, the Poly-A particles in a single administration are non-uniform in size, shape and surface morphology. In some embodiments, fabrication parameters, e.g., emulsification speed and oil phase polymer concentration, are adjusted to achieve the desired average Poly-A particle sizes e.g., 200 nm and 2 μm. Scanning electron microscopy (SEM) images of the dried particles are used to evaluate particle surface morphology, and the particle size and zeta potential (ZP; a measure of surface charge) determined using a Malvern Zetasizer Nano-ZS. In particular embodiments, Poly-A particle degradation profiles are determined in phosphate buffer (PBS) and plasma at pH 7.4 and 37° C. via a spectrophotometer (FIG. 1C), and changes in the solution pH are monitored as the Poly-A particles degrade. In additional embodiments, Poly-A particle dimensions, morphology, uniformity and shape are quantified by flow cytometry, and optimized for the capacity to bind human umbilical vein endothelial cells from the flow of whole blood (e.g., human whole blood) to predict in vivo functionality.

Figure 2:
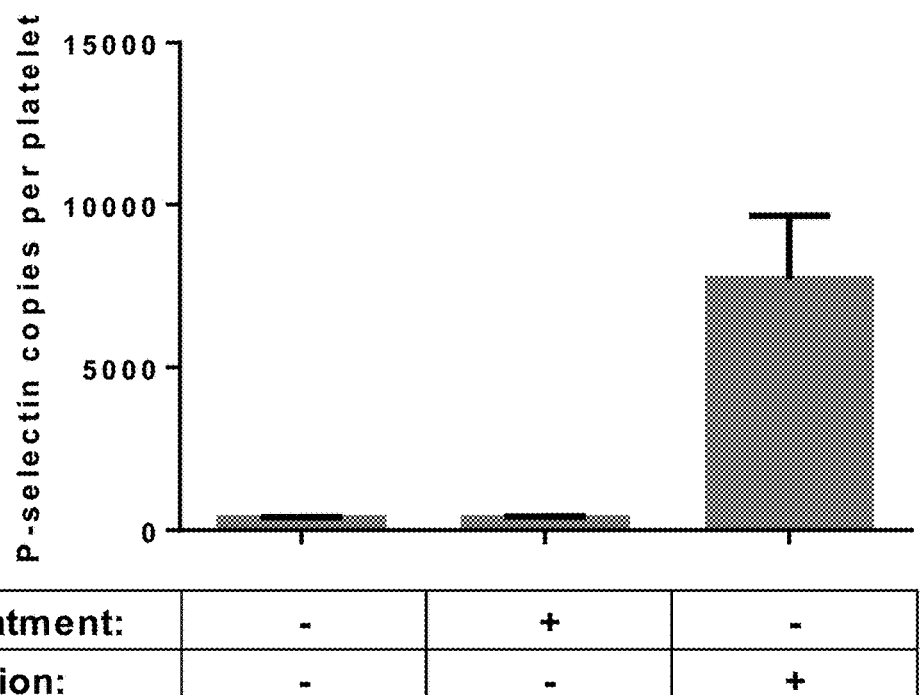
FIG. 2: Shows P-selectin expression by resting human platelets with or without Poly-A particle incubation relative to agonist (ADP) activated platelets. Poly-A non-targeted microparticles do not activate human platelets, thereby demonstrating hemocompatibility.

In some embodiments, the hemo-compatibility of Poly-A particles with human cells is optimized in vitro. In certain embodiments, the potential for Poly-A particle toxicity in blood is evaluated and optimized via assays of platelet activation and hemolysis. For platelet activation assays, Poly-A particles are incubated for 1 hr in platelet rich plasma (PRP) obtained via centrifugation of whole blood. The PRP samples exposed to Poly-A particles are then stained with anti-CD41/61 (PE) and anti-CD62P (APC) to determine P-selectin expression via flow cytometry. P-selectin expression on resting platelets is minimal, and its high expression on platelets is a sign of activation. For hemolysis assays, Poly-A particles are with isolated human RBCs in PBS buffer for 15, 30, 60 and 120 min, after which the sample is centrifuged to pellet intact RBCs and particles. The supernatant from the Poly-A particle incubated sample is evaluated for hemoglobin concentration as an indication of RBC lysis via spectrophotometer. Non-targeted Poly-A microparticles do not activate human platelets (FIG. 2), or induce hemolysis when placed in human blood.

In some embodiments, elements of the Poly-A particles of the present invention are optimized for preferred in vivo biodistribution and biocompatibility by visualization of Poly-A microparticle adhesion to inflamed venules in experimental animal models of human diseases and conditions, together with healthy control animals. Adherence to inflamed vessel wall in vivo is detected with a fluorescent label within the Poly-A particle matrix. Using intravital microscopy (IVM) to visualize the adhesion of Poly-A particles, their impact on the adhesion of circulating neutrophils is evaluated in vivo. Healthy C57BL/6J mice of mixed sex (50:50) are used. In control assays, (1) Poly-A particles are observed in non-inflamed mice (negative), and neutrophil adhesion is quantified in mice with mesentery inflammation but no particles (i.e., vehicle only) injected. Poly-A particles in mice with inflammation are evaluated. Poly-A particles are targeted via anti-ICAM-1 (YN1/1.7.4; murine) antibody at 10,000 sites/$\mu m^2$. This antibody density is sufficient to mediate firm arrest of microspheres to the inflamed vessel wall in vivo. Particles are injected in sterile PBS at ~15-mg/kg, to yield a human equivalent dose of ~1.2-mg/kg or ~45-mg/$m^2$ which is sufficient for reducing neutrophils in BALF in ALI mice. This dose aligns with the preclinical dosages evaluated in mice, and Phase II human clinical trials have routinely employed between 35 and 50 mg/$m^2$ dose of pegylated liposomal doxorubicin.

In a mesentery inflammation model, mice are anesthetized, and a lateral tail vein catheter is placed for intravenous injection of antibodies, particles and additional anesthetic reagents as needed. The mice are placed on a microscope with a heated stage at 37° C., and the mesentery is exteriorized to a glass coverslip via a midline incision. Following vessel selection, to confirm that neutrophils are the predominant cells blocked from adhering to the inflamed vessels, neutrophils are tagged in vivo by direct injection of fluorescent Ly6G antibody (5 µg of Gr-1 or 1A8) before particle injection. Acute inflammation is induced by topical application of TNF-α-10 µL of 200 µg/mL in PBS. Particles are injected at 10 min after TNF-α activation. The mesentery vessels are imaged for particle and cell adhesion up to 60 min via a 25×oil objective, inverted fluorescence microscope (Zeiss Axio Observer Z1 Marianas Microscope). Images are recorded continuously in brightfield and green fluorescence every 10 ms using Slidebook 6 software. Data on Poly-A particle adhesion and neutrophil blocking is collected at <5, 10, 15, and 60 min after particle injection. At 60 min, multiple vessels are imaged within the same animal for up to 2 min each to ensure any observed particle adhesion and neutrophil blocking is not an artifact of the single vessel chosen for imaging. At the end of the IVM imaging, mice are euthanized, and the Poly-A particle distribution in vital organs is evaluated, e.g., in lungs, liver, heart, kidney, and spleen, and compared between the inflamed and non-inflamed mice. Whole-organ scans rating relative total fluorescence are obtained using an Odyssey CLx Infrared Imaging System (LI-COR), and then single cell suspensions of all organs are obtained via a collagenase homogenization analyzed via cytometry. Homogenized liver samples are evaluated for changes in leukocyte population and cytokines.

In some embodiments, elements of the Poly-A particles of the present invention are optimized for preferred in vivo blood circulation and clearance. Kinetics assays in healthy mice are conducted wherein mouse blood is sampled at 5 min, 15 min and 0.5, 1, 2, 4, 6, 12, and 24 hr after Poly-A particle injection (at, for example) 15 mg/kg), and evaluated for particle counts in order to characterize the clearance rate of Poly-A particles from the bloodstream. In certain embodiments, a Poly-A particle is made with an ICAM-1 antibody, and elements of the Poly-A particles are evaluated and compared. Control mice comprise mice treated with PBS only, and mice treated with non-targeted, 2 µm Poly-A particles. At the desired time, 10 µL of blood are collected and scanned for Poly-A particles (e.g., by fluorescent scanning) on an Odyssey CLx Infrared imaging system. Values for pharmacokinetic parameters such as plasma half-life, distribution volume, and clearance are obtained from the plot of plasma concentration versus time profiles using the PKSolver, with the data fitted with a 2-compartment model.

At 24 hrs after particle injection, mice are euthanized, and particle distribution and cytokine levels are evaluated in critical organs that have been extracted. Portions of the vital organs are subjected to hematoxylin and eosin (H&E) staining and are blindly scored by a clinical veterinary pathologist for any sign of tissue damage/inflammation associated with injection of Poly-A particles.

In some embodiments, elements of the Poly-A particles of the present invention are optimized for preferred profiles of biocompatibility in healthy mice. Poly-A particle injections described above are performed, and blood cell counts are measured. Mice are euthanized either at 2-, 30-, 60-min after particle injection, or are returned to their cages and observed for weight and behavioral changes over 7 days relative to their baseline before particle injection. The time points are chosen based on evidence that the neutrophil counts return to baseline by 1 hr after particle injection when particles are cleared from the bloodstream. At the targeted time interval, mice are euthanized via cardiac puncture for blood collection and vital organs removed. Blood for cell counts (platelets, neutrophils, monocytes, and lymphocytes), and hematocrit and hemoglobin levels relative to PBS control mice are measured, together with levels of platelet activation and cellular apoptosis. The weight of each organ is recorded, and particle composition is assessed in tissue homogenates. Histology is used to detect whether or not there is injury or scaring in vital organs. Signs of inflammation are evaluated via measurement of cytokine expression levels. Experiments conducted in the course of development of the present invention show that (1) Poly-A particles bind to the inflamed vessel and reduce neutrophil adhesion, and (2) Poly-A particles display minimal toxicity in mice; 100% of mice with LPS-induced ALI survive to at least 48 hrs after Poly-A particle injection. In other embodiments, anti-ICAM-1 coated Poly-A is used. In other embodiments, alternative routes or administration are used including, for example, intravascular administration, intra-arterial administration, intravenous administration, catheter-directed administration, pulmonary artery catheter directed administration, interventional radiology administration, ultrasound guided administration, MRI guided administration, surgically guided administration, laparoscopically guided administration, bronchoscopically guided administration, intratracheal administration, intramuscular administration, subcutaneous administration, enteral administration, rectal administration, inhaled administration, intraperitoneal administration, intra-articular administration, intraspinal administration, intracerebroventricular administration, intravessicular administration, intraparenchymal administration, and the like. In other embodiments, samples are incubated with an antibody against the isotype of the anti-ICAM-1 bound to Poly-A VTP.

In some embodiments, elements of the Poly-A particles of the present invention are optimized for their therapeutic benefit. In certain embodiments, the therapeutic impacts of Poly-A particles are compared in a *Pseudomonas* (*P.*) *aeruginosa* mouse model of ARDS. *P. aeruginosa*, a gram-negative bacterium, is the second most common cause of pneumonia in hospitalized patients causing lung injury with a mortality rate of 60-90% in mechanically ventilated patients. A mouse model of *P. aeruginosa*-induced lung injury replicates the histological and immunological features of ARDS in humans; 46-51% of ARDS in humans arise from a pulmonary bacterial infection. The model evaluates the protective effects of the Poly-A particles on lung injury along with possible detrimental effects of the particles on innate protective responses. C57BL/6J mice of mixed sex (50:50) strain, and 19660 of *P. aeruginosa* obtained from ATCC, are used.

In some embodiments, elements of the Poly-A particles of the present invention are optimized for the timing of neutrophil transmigration and barrier disruption. The time course of neutrophil emigration into the lungs is evaluated after *P. aeruginosa* administration in mice in the absence of Poly-A particles to establish a baseline to guide the timing of Poly-A particle interventions. Experimental Example 2 shows the importance of the "time after infection" at which Poly-A particles are injected for achieving a significant therapeutic benefit (FIG. 5) linked to the kinetics of neutrophil migration into the BALF and onset of lung injury. Mice are infected with *P. aeruginosa* and the time at which mice are euthanized is varied e.g., at 6 hrs, 12 hrs, 18 hrs, 24 hrs, 30 hrs and 36 hrs after bacterial infection. The 36 hrs upper boundary is chosen in view of 20% survival at 48 hrs after *P. aeruginosa* infection for C57BL/6J mice, with ~70% survival at 24 hr. The BALF, lung tissue and blood are analyzed for cellular content, bacterial (CFU) and inflammation markers. Leukocyte counts are obtained via flow cytometry wherein the BALF single-cell suspension or blood is stained with a panel of fluorescent antibodies to identify different cell populations. Neutrophils, monocytes, lymphocytes, macrophages and dendritic cells are stained in the BALF. Changes in the levels of inflammatory cytokines (e.g., IL-6, IL-12, MIP-2, MCP-1, IL-17 KC, IL-10, TNF-α, and IL-1B) in the BALF supernatant and plasma via ELISA are compared. BALF albumin and IgM levels are quantified to evaluate alveolar epithelial integrity in infected mice. Major organs, e.g., lungs, liver, heart, kidney, and spleen, are harvested and evaluated for bacterial CFUs, leukocytes and inflammatory cytokines. All observed cell counts and cytokine levels are compared to the baseline in non-infected (vehicle only) mice.

Figure 6:
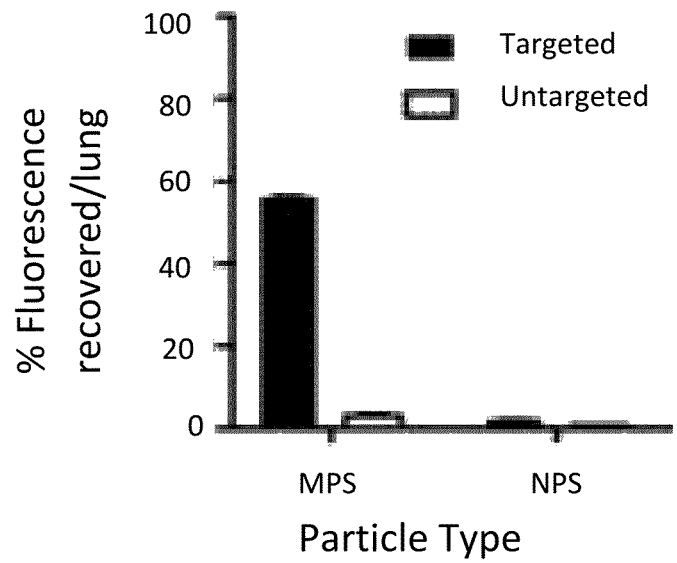
FIG. 6: Shows accumulation of anti-intracellular adhesion molecule (ICAM)-1 targeted (shaded) and non-targeted PS MPs in the lung 24 hr after tail vein injection.
Figure 7:
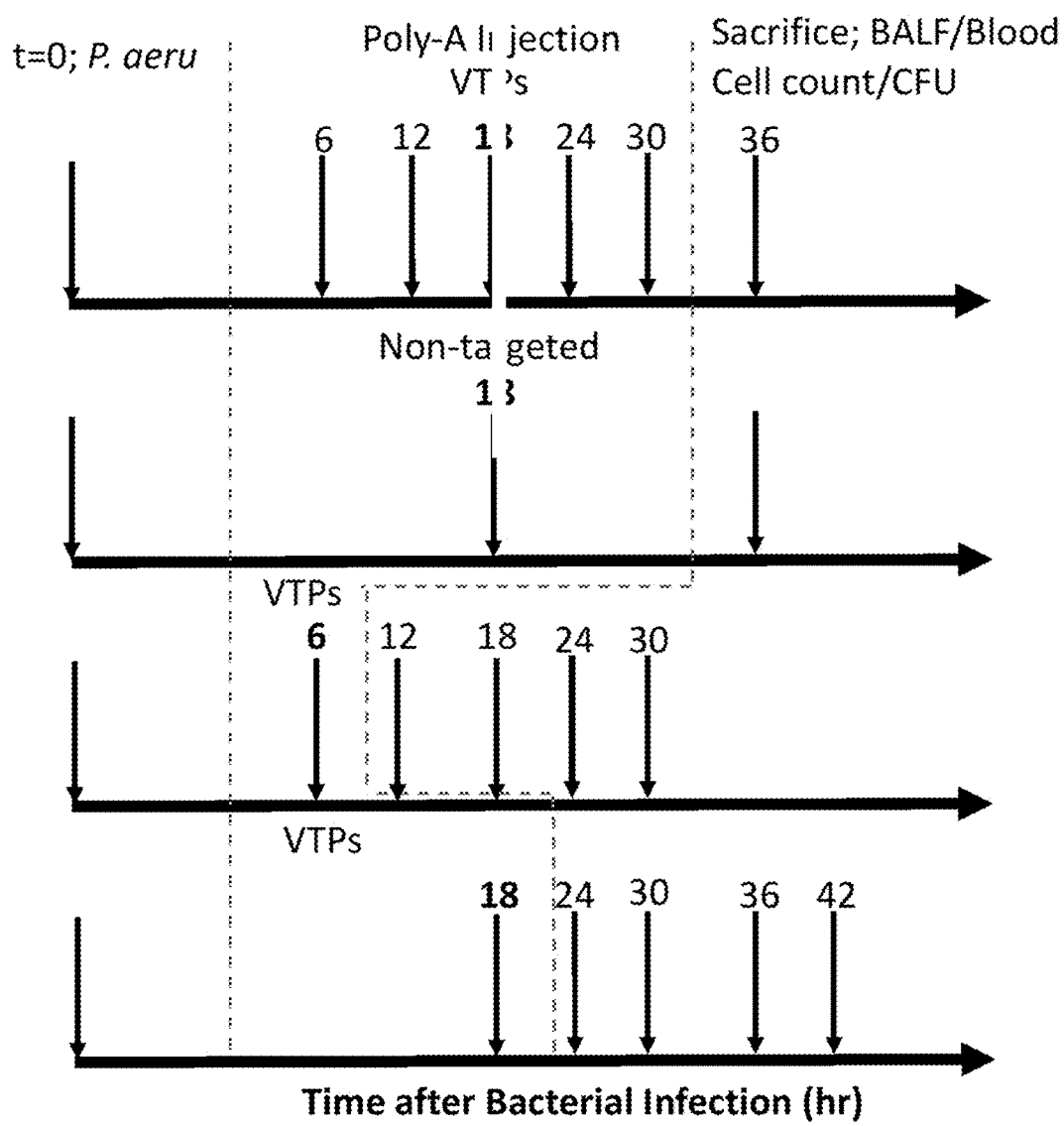
FIG. 7: Shows proposed timelines for mice particle injections and tissue harvest relative to the timing of P. aeruginosa infection.

In some embodiments, elements of the Poly-A particles of the present invention are optimized for the impact of timing of Poly-A particle administration on reducing lung injury in *P. aeruginosa*-induced ALI/ARDS. The capacity of Poly-A particles to ameliorate lung injury in *P. aeruginosa* infected mice vs. the extent of injury characterized for the "no particle" treatment is compared via evaluation of leukocyte count, cytokine levels, and bacteria CFU in the BALF and lungs, blood, and other major organs. VTPs of different diameter (e.g., 200 nm and 2 μm VTPs with murine anti-ICAM-1 (YN1/1.7.4)) are evaluated. PS VTPs coated with this antibody are retained in lungs of ALI-mice for up to 24 hrs unlike untargeted microparticles (FIG. 6). Mice are treated with VTPs (at, for example 15 mg/kg or other dose), injected at varying times of 6 hrs, 12 hrs, 18 hrs, 24 hrs and 30 hrs after infection. Regardless of the particle injection interval, mice are euthanized at a fixed 36 hrs after interval after infection (FIG. 7). The capacity of Poly-A particles antibody-targeted (anti-ICAM-1 or anti-E-selectin or anti-VCAM-1) to enhance therapeutic impact is evaluated by comparison with administration of non-targeted, 2 μm Poly-A at the 18 hr point shown to reduce BALF neutrophils and blood CFU in *P. aeruginosa*-infected mice (Example 2). BALF cells are counted, and changes in albumin/IgM levels, bacteria CFU, and inflammatory cytokines in the BALF supernatant relative to the Poly-A injection time are measured. Lung tissue is assessed for particle content (i.e., by whole organ scan histology, and tissue homogenate), as well as for bacterial CFUs, cytokines and leukocyte count. The degree of lung injury, via blind scoring of H&E stained lung sections for epithelial thickening, airway epithelial necrosis, and intra-alveolar edema is assessed for the different MP injection times in comparison to the "no-microparticle" controls.

In some embodiments, elements of the Poly-A particles of the present invention are optimized for the time after particle injection at which animals are euthanized by comparison of the extent of lung injury and bacteria dissemination observed. Poly-A particles of 2 μm size are administered at a fixed "time after infection" of 6 hrs and 18 hrs, and the BALF and major organ cells/cytokine/CFU/particles counts are be analyzed (i.e., mice are euthanized) at varying times of 6 hrs, 12 hrs, 18 hrs, and 24 hrs after particle injection (FIG. 7). The liver is evaluated to determine if the injection of Poly-A particles with diverse elements promotes accumulation of neutrophils and particles and injury to the liver in the ALI/ARDs mice. A whole organ scan of a fraction of the liver is used for detection of particle localization. A section of the liver is homogenized and evaluated for particles, leukocyte population, and expression of inflammation-associated cytokines. The structure of the liver tissue/cells is assessed via H&E staining, and liver function tests are performed (LFTs) on serum from the blood collected at euthanasia, including aspartate aminotransferase, alkaline phosphatase bilirubin, and alanine aminotransferase as a further measure of potential liver damage by particles in the ALI model. Controls are livers from ALI/ARDs mice with no particle treatment and the vehicle control.

In some embodiments, compositions of the Poly-A particles of the present invention are optimized for therapeutic benefit. The added benefits of SA released from Poly-A particles are evaluated for changes in BALF cell counts and cytokine levels by varying the rate of the Poly-A polymer degradation, from non-degrading polymers to polymers that substantially degrade within days. FIG. 8 shows the structure of a Poly-A polymer, wherein "R" corresponds to linkers that range from linear hydrocarbons, e.g. $(CH_2)_3$, to branched aliphatics, and "n" is a polymer repeat unit. Particles fabricated from Poly-A polymers with the R1 and R2 adipic acid linker degrade completely in 3 and 21 days, respectively (Rosario-Melendez, R., M. A. Ouimet, and K. E. Uhrich, Formulation of salicylate-based poly(anhydride-ester) microspheres for short- and long-term salicylic acid delivery. Polym Bull (Berl), 2013. 70(1): p. 343-351.) Particles with the R3 linker release 21% of their SA over 21 days and reach complete degradation within 3.5 months. In certain embodiments, both "R" and "n" are tuned to achieve polymers for formulating 2 μm VTPS that substantially degrade in 3 days (R1), 7 (R2), 21 (R2-baseline polymer), and >28 (R3) days. (Prudencio, A., R. C. Schmeltzer, and K. E. Uhrich, Effect of Linker Structure on Salicylic Acid-Derived Poly(anhydride-esters). Macromolecules, 2005. 38(16): p. 6895-6901.) In some embodiments, a Poly-A particle degradation profile is determined via assays with microspheres that degrade in plasma. Particles are added to plasma at a concentration based on the fraction of particles injected identified in the lungs. Poly-A particles of varying degradation rates are fitted with anti-ICAM-1 antibody and injected into *P. aeruginosa* infected mice at 18 hrs after infection. Mice are euthanized 24 hrs after infection. Blood, BALF, and tissues are harvested, and the impact of the Poly-A degradation rates on the cell counts, cytokine and protein levels, and bacteria CFU are measured. Controls are infected mice treated with (1) aspirin in DMSO (100 μg/g), (2) DMSO only, (3) non-degrading polystyrene (PS) particles, and (4) degrading PLGA particles that release lactic acid instead of the SA.

Figure 9:
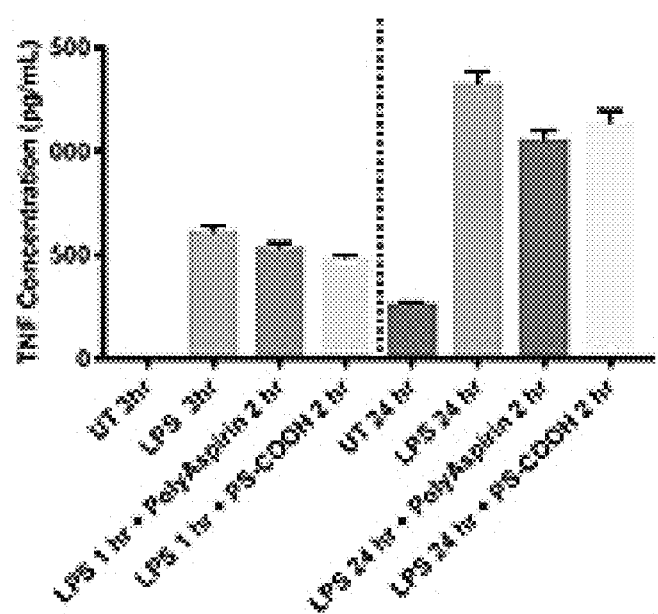
FIG. 9: Shows TNF-α secretion by alveolar macrophages cultured for 2 hrs or 24 hrs and then exposed to Poly-A or PS MPs relative to untreated (UT) macrophages.

In some embodiments, elements of the Poly-A particles of the present invention are optimized for neutrophil phagocytosis, e.g. rod shape. Surface protein expression and cytokine secretion by primary blood leukocytes (e.g., neutrophils, monocytes, and lymphocytes) are measured with or without exposure to Poly-A particles. Mouse whole blood and isolated cells are incubated with, for example, 3- and >28-day degrading Poly-A particles for 1 hr. The particle-incubated cells are analyzed via flow cytometry to measure the amount of Poly-A particles internalized, and the expression levels of LAMs, e.g., CD26L, CD15, CD11b, and CD66b, via fluorescent antibody staining. Additionally, leukocytes are evaluated for apoptosis markers, including annexin V, caspase, and phosphatidylserine. The supernatant is characterized via ELISA for pro-inflammatory factors released by isolated cells after phagocytosis. Controls are blood/cells exposed to PS particles and to vehicle (no particles). The supernatant obtained from particle-treated, isolated primary cells are used to treat macrophages and dendritic cells (DCs) isolated from the lungs to identify factors secreted from Poly-A particle-exposed neutrophils (or monocyte or lymphocytes) associated with an anti-inflammatory phenotype compared to PS particle or vehicle-only controls. Mouse lung macrophage expression of inflammatory cytokines is not altered when incubated with Poly-A directly FIG. 9). Lung macrophages and DCs are isolated from dispersed lung digest cells. (Deng, J. C., G. Cheng, M. W. Newstead, X. Zeng, K. Kobayashi, R. A. Flavell, and T. J. Standiford, Sepsis-induced suppression of lung innate immunity is mediated by IRAK-M. J Clin Invest, 2006. 116(9): p. 2532-42.) Isolated macrophages and DCs are treated with LPS (1 hr), or culture with *P. aeruginosa* (8 hr), before exposure to cell-released supernatant for an additional 2 hr. Control assays are untreated and LPS only/*P. aeruginosa* macrophages and DCs. The macrophage and DC supernatant is evaluated factors secreted in ALI/ARDS, including IL-6, IL-10, IP-10, KC, MCP-1, MIP2, and TNF-α.

In some embodiments, polymer particles of the present invention comprise Poly-A polymer particles. In other embodiments, polymer particles comprise PLGA polymer particles. Polymer particles of the present invention are not confined to Poly-A, PS or PLGA particles. In particular embodiments, polymer particles comprise additional polymers that are biodegradable, targetable, and configured for microparticle and/or nanoparticle administration.

In some embodiments, the Poly-A particles of the present invention are generated using an emulsion solvent evaporation method. In certain embodiments, polyvinyl alcohol (PVA) (for example, 87-90% hydrolyzed PVA with an average Mw of 20-70 dDa), is dissolved in water to provide a 1 wt % PVA solution of pH 6-7. Poly-A (for example, 20 mg of Poly-A) is dissolved in dichloromethane (DCM), and the Poly-A in DCM oil phase is slowly added to the PVA water phase during mixing at 4000 rpm or greater for 1-2 hrs or longer. Particles generated are then centrifuged, and the PVA/water solution is aspirated. The pellet is resuspended in deionized water, washed, frozen under liquid nitrogen, lyophilized and stored at −20° C.

In some embodiments, the Poly-A particles of the present invention are modified to be carriers of one or more bioactive compounds or drugs. In certain embodiments, emulsion solvent evaporation (ESE) techniques are used to fabricate drug loaded degradable microparticles, for example, microspheres from the Poly-A polymer. For hydrophobic compounds and drugs a single emulsion process is used wherein the compound or drug is added to Poly-A polymer (Mw=~20 kDa) dissolved in dichloromethane (oil phase), and the solution is emulsified into a solution of 1 wt % PVA in water. The oil phase (poly-A and compound or drug) is slowly injected via a syringe needle, and the emulsion is stirred continuously for up to 2 hrs, allowing the oil droplets to harden. The resultant Poly-A particles are washed twice via centrifugation and dried via lyophilization. Particles are stored at −40° C. until use. For hydrophilic drugs, a double emulsion process (water in oil in water) is used. The compound or drug is added to a water phase that is emulsified into the Poly-A polymer dissolved in dichloromethane. The drug-polymer emulsion is then be emulsified into a solution of 1 wt % PVA in water.

Pharmaceutical compositions that include at least one Poly-A particle described herein and at least one pharmaceutically acceptable carrier may also include one or more other active agents. The Poly-A particles described herein can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the Poly-A particles described herein can be formulated: (a) for administration selected from any of oral, pulmonary, intravenous, intra-arterial, intrathecal, intra-articular, rectal, ophthalmic, colonic, parenteral, intracisternal, intravaginal, intraperitoneal, local, buccal, nasal, and topical administration (for example, dermatologic, mucosal, conjunctival and/or internal topical administration); (b) into a dosage form selected from any of liquid dispersions, gels, aerosols, ointments, creams, tablets, sachets and capsules; (c) into a dosage form selected from any of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi. The term "stable", as used herein, means remaining in a state or condition that is suitable for administration to a subject.

The carrier can be a solvent or dispersion medium, including, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., a Poly-A particle) in an appropriate amount in an appropriate solvent with one or a combination of ingredients enumerated above, as desired, followed by filtered sterilization. Generally, dispersions are prepared by incorporating at least one Poly-A particle into a sterile vehicle that contains a basic dispersion medium and any other desired ingredient. In the case of sterile powders for the preparation of sterile injectable solutions, exemplary methods of preparation include vacuum drying and freeze-drying, both of which will yield a powder of a Poly-A particles plus any additional desired ingredient from a previously sterile-filtered solution thereof. Oral compositions generally include an inert diluent or an edible carrier. They can be enclosed, for example, in gelatin capsules or compressed into tablets. For the purpose of oral therapeutic administration, the Poly-A particles can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from a pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In some embodiments, a Poly-A particle is prepared with a carrier that protects against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of a Poly-A particle may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

In some embodiments, it is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a Poly-A particle calculated to produce the desired therapeutic effect in association with the required pharmaceutical carrier. The specification for the dosage unit forms of Poly-A particles described herein are dictated by and directly dependent on the characteristics of the particular Poly-A VTP and the particular therapeutic effect to be achieved, and the limitations inherent in the art of compounding such an active agent for the treatment of individuals.

Pharmaceutical compositions comprising at least one Poly-A particle can include one or more pharmaceutical excipients. Examples of such excipients include, but are not limited to, binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as AVICEL. PH101 and AVICEL. PH102, silicified microcrystalline cellulose (ProSolv SMCC), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, crospovidone, sodium starch glycolate, and mixtures thereof; (4) lubricants, including agents that act on the flowability of a powder to be compressed, include magnesium stearate, colloidal silicon dioxide, such as AEROSIL 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as AVICEL PH101 and AVICEL. PH102; lactose such as lactose monohydrate, lactose anhydrous, and PHARMATOSE. DCL21; dibasic calcium phosphate such as EMCOMPRESS; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, MAGNASWEET (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the formulations described herein are substantially pure. As used herein, "substantially pure" means the active ingredient (e.g., Poly-A particle) is the predominant species present (i.e., on a molar basis it is more abundant than any other individual species in the composition). In one embodiment, a substantially purified fraction is a composition wherein the active ingredient comprises at least about 50 percent (on a molar basis) of all macromolecular species present. Generally, a substantially pure composition will include more than about 80% of all macromolecular species present in the composition. In various embodiments, a substantially pure composition will include at least about 85%, at least about 90%, at least about 95%, or at least about 99% of all macromolecular species present in the composition. In various embodiments, the active ingredient is purified to homogeneity (contaminant species cannot be detected in the composition by conventional detection methods) wherein the composition consists essentially of a single macromolecular species.

Kits Comprising Poly-A Polymer Particle Compositions

The present disclosure provides kits comprising any of the Poly-A particles described herein. Such kits can comprise, for example, (1) at least one Poly-A particle; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

In certain embodiments, the present invention provides instructions for administering said inhibitors of inflammation (e.g., a Poly-A) to a subject. In certain embodiments, the present invention provides instructions for using the compositions contained in a kit for the treatment of conditions characterized by inflammation in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat a variety of medical conditions associated with inflammation (e.g., ALI/ARDS, sepsis, infection, arthritis, rheumatoid arthritis, juvenile rheumatoid arthritis). In certain embodiments, the present invention provides instructions for using the compositions contained in the kit to treat a variety of medical conditions associated with inflammation, and/or autoimmune conditions.

Methods of Treatment

In some embodiments, provided herein are methods of preventing or treating (e.g., alleviating one or more symptoms of) medical conditions through the use of a Poly-A particle. The methods comprise administering a therapeutically effective amount of a Poly-A particle to a subject in need thereof. The described Poly-A particles can also be used for prophylactic therapy. In some embodiments, the Poly-A particle is administered intravenously. Poly-A particles used in methods of treatment can be a Poly-A VTP or nTP described herein, or a pharmaceutically acceptable salt thereof, or a prodrug thereof. The individual or subject can be any animal (domestic, livestock or wild), including, but not limited to, cats, dogs, horses, pigs and cattle, and preferably human subjects. As used herein, the terms patient, individual, and subject may be used interchangeably.

As used herein, "treating" describes the management and care of a patient for the purpose of treating a disease, condition, or disorder and includes the administration of a Poly-A particle to prevent the onset of the symptoms or complications of a disease, condition or disorder; to alleviate symptoms or complications of the disease, condition, or disorder; or to eliminate the presence of the disease, condition or disorder in the patient. More specifically, "treating" includes reversing, attenuating, alleviating, minimizing, suppressing or halting at least one deleterious symptom or effect of a disease (disorder) state, disease progression, disease causative agent or other abnormal condition. Treatment is generally continued as long as symptoms and/or pathology ameliorate.

In some embodiments, compositions and methods of the present invention are used to prevent, treat, and/or ameliorate inflammatory diseases, malignant diseases, infections, autoimmune diseases, and/or other diseases or conditions in which neutrophil pathophysiology is implicated. Non-limiting exemplary inflammatory diseases that may be treated with the Poly-A particles described herein include rheumatoid arthritis, juvenile idiopathic arthritis, systemic-onset juvenile idiopathic arthritis, gout, osteoarthritis, sepsis, asthma, interstitial lung disease, inflammatory bowel disease, systemic sclerosis, intraocular inflammation, Grave's disease, endometriosis, systemic sclerosis, adult-onset still disease, amyloid A amyloidosis, polymyalgia rheumatic, remitting seronegative symmetrical synovitis with pitting edema, Behcet's disease, uveitis, graft-versus-host diseases, and TNFR-associated periodic syndrome. Malignant diseases that may be treated with the Poly-A particles described herein include cancers and cancer-related conditions. Non-limiting exemplary cancers include multiple myeloma, leukemia, pancreatic cancer, breast cancer, colorectal cancer, cachexia, melanoma, cervical cancer, ovarian cancer, lymphoma, gastrointestinal, lung cancer, prostate cancer, renal cell carcinoma, metastatic kidney cancer, solid tumors, non-small cell lung carcinoma, non-Hodgkin's lymphoma, bladder cancer, oral cancer, myeloproliferative neoplasm, B-cell lymphoproliferative disease, and plasma cell leukemia. Non-limiting exemplary cancer-related conditions include non-small cell lung cancer-related fatigue and cancer related anorexia. Non-limiting exemplary infections that may be treated with the Poly-A particles described herein include bacterial infections, viral infections, fungal infections, rickettsial infections, parasitic infections, human immunodeficiency virus (HIV) infections, human T-lymphotropic virus (HTLV) infections, respiratory virus infections, cerebral malaria, urinary tract infections, and meningococcal infections. Non-limiting exemplary autoimmune diseases that may be treated with the Poly-A VTPs described herein include systemic lupus erythromatosus, systemic sclerosis, polymyositis, vasculitis syndrome including giant cell arteritis, Takayasu aeteritis, cryoglobulinemia, myeloperoxidase-antineutrophil cytoplasmic antibody-associated crescentic glomerulonephritis, rheumatoid vasculitis, Crohn's disease, relapsing polychondritis, acquired hemophilia A, and autoimmune hemolytic anemia. Further diseases that may be treated with the Poly-A particles described herein include, but are not limited to, Castleman's disease, ankylosing spondylytis, coronary heart disease, cardiovascular disease in rheumatoid arthritis, pulmonary arterial hypertension, chronic obstructive pulmonary disease (COPD), atopic dermatitis, psoriasis, sciatica, type II diabetes, obesity, giant cell arteritis, acute graft-versus-host disease (GVHD), non-ST elevation myocardial infarction, anti-neutrophil cytoplasmic antibody (ANCA) associated vasculitis, neuromyelitis optica, chronic glomerulonephritis, and Takayasu arteritis.

In some embodiments, the disclosed compounds or pharmaceutically acceptable salts thereof, or prodrugs, can be administered in combination with other active agents. Compositions including the disclosed Poly-A particles may contain, for example, more than one Poly-A particle. In some embodiments, a composition containing one or more Poly-A particles are administered in combination with one or more additional agents for preventing, treating, and/or ameliorating inflammatory diseases, malignant diseases, infections, autoimmune diseases, and/or other diseases or conditions in which neutrophil pathophysiology is implicated.

The dosage regimen utilizing the Poly-A particles is selected in accordance with a variety of factors, including, for example, type, species, age, weight, sex and medical condition of the subject; the severity of the condition to be treated; the route of administration; the renal and hepatic function of the subject; and the particular Poly-A particle or carrier thereof employed. An ordinarily skilled physician or veterinarian can readily determine and prescribe the effective amount of the composition required to prevent, counter or arrest the progress of the condition. In general, the dosage, i.e., the therapeutically effective amount, ranges from about 1 ng/kg to about 1 g/kg body weight, in some embodiments about 1 µg/kg to about 1 g/kg body weight, in some embodiments about 1 ug/kg to about 100 mg/kg body weight, in some embodiments about 1 µg/kg to about 10 mg/kg body weight of the subject being treated, per day.

Methods for Diagnosing and Detecting

Poly-A particles, described herein, find use as diagnostic reagents, either in vitro or in vivo. The Poly-A particles identified herein can be used in any diagnostic, detection, imaging, high throughput screening or target validation techniques or procedures or assays for which Poly-A particles without limitation can be used.

Poly-A particles capable of binding restraining neutrophils, described herein, find use in a variety of assays including, assays that use planar arrays, beads, and other types of solid supports. The assays may be used in a variety of contexts including in life science research applications, clinical diagnostic applications, (e.g., a diagnostic test for a disease, or a "wellness" test for preventative healthcare), affinity-linked oligonucleotide nuclease assay (ALONA) and ubiquitin-proteasome system (UPS) assays, and in vivo imaging applications. For some applications, multiplexed assays employing the described Poly-A VTPs and may be used.

In some embodiments, the Poly-A particles are used as sensitive and specific reagents for incorporation into a variety of in vitro diagnostic methods or kits. In some embodiments, the Poly-A particles are used as substitutes for antibodies in a number of infectious, or other type of disease detection methods where the Poly-A particle includes either or both a detectable material and an immobilization or capture component. In these embodiments, after the Poly-A particle from the kit is mixed with a clinical specimen, a variety of assay formats may be utilized. In one embodiment, the Poly-A particles also include a detectable label, such as a fluorophore. In other embodiments, the assay format may include fluorescence quenching, hybridization methods, flow cytometry, mass spectroscopy, inhibition or competition methods, enzyme linked oligonucleotide assays, SPR, evanescent wave methods, etc. In some embodiments, the Poly-A particle is provided in the kit in solution. In other embodiments, the Poly-A particle in the kit is immobilized onto a solid support used in conjunction with the assay for testing the specimen. In various embodiments, the solid support is designed for the detection of one or more targets of interest. In other embodiments, the kit may further include reagents to extract the target of interest, reagents for constructing Poly-A particles, reagents for performing washing, detection reagents, etc.

Diagnostic or assay devices, e.g. columns, test strips or biochips, having one or more Poly-A particles adhered to a solid surface of the device are also provided. The Poly-A particles may be positioned so as to be capable of binding neutrophils that are contacted with the solid surface to form Poly-A particle-neutrophil complex that remains adhered to the surface of the device, thereby capturing the target and enabling detection and optionally quantitation of the target. An array of Poly-A particles (which may be the same or different) may be provided on such a device.

In one embodiment for detecting neutrophils, a Poly-A particle is contacted with a labeling agent that includes a binding partner that is specific for a neutrophil. The specific binding partner may be any suitable moiety, including an antibody, an antibody fragment, a synthetic antibody mimetic, a biomimetic, an aptamer, a molecular imprinted ligand, and the like. The specific binding partner is conjugated or linked to another labeling agent component, usually, a detectable moiety or label.

The detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

EXAMPLES

The invention, now being generally described, will be more readily understood by reference to the following examples, which are included merely for purposes of illustration of certain aspects and embodiments of the present invention, and are not intended to limit the invention. All protocols for animal and human studies were approved by the University of Michigan's Committee on Use and Care of Animal or the Institutional Review Board.

Example 1—Poly-A Particles Reduce Neutrophil Lung Migration in ALI

Figure 3:
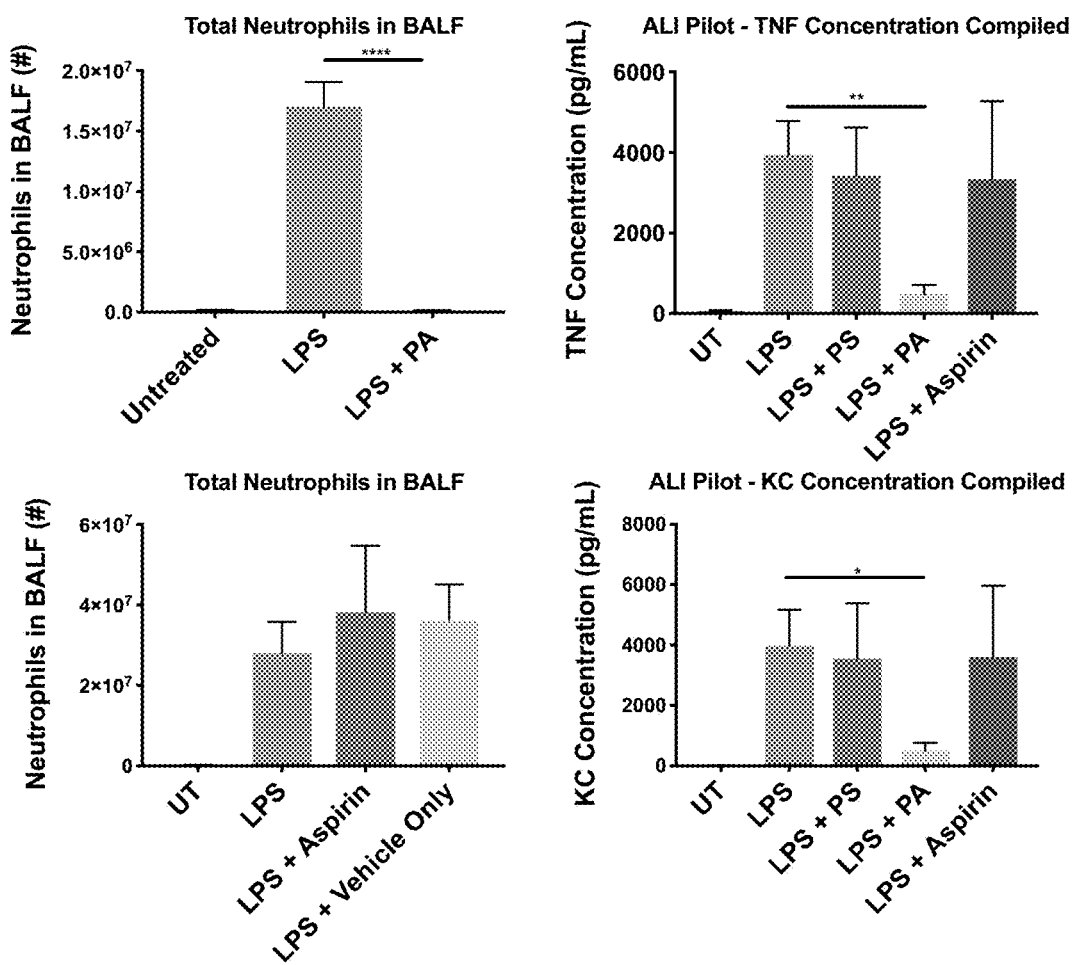
FIG. 3: Shows neutrophil counts and cytokine concentrations in lung bronchoalveolar lavage fluid (BALF) of untreated (UT) and lipopolysaccharide (LPS)-treated (ALI) mice. PA=Poly-A particles, PS=Polystyrene particles. Mouse treatments are provided on the X axis.

Poly-A microspheres were injected into the tail vein of mice with LPS-induced ALI at 30 mg/kg. Poly-A spheres injected 1 hr after LPS administration significantly reduced the BALF neutrophil count compared to ALI mice with no particles (FIG. 3). Tail vein injection of aspirin in DMSO did not reduce the BALF neutrophil count in ALI mice, demonstrating the utility of the Poly-A VTP particle-neutrophil physical interaction in the observed reduction of neutrophil lung migration in ALI. Particle-treated ALI mice had lower albumin levels in the BALF (FIG. 16), denoting a reduction of lung injury with particle injection. The levels for markers of inflammation typically found in the BALF in ALI mice, showed that the Poly-A spheres reduce inflammation in lung significantly (p<0.05) compared to PS or aspirin. BALF concentration of TNF-α, KC (FIG. 15), and MIP2 (FIG. 16) were reduced in Poly-A-treated ALI-mice, but not for mice treated with PS spheres or aspirin.

Figure 4:
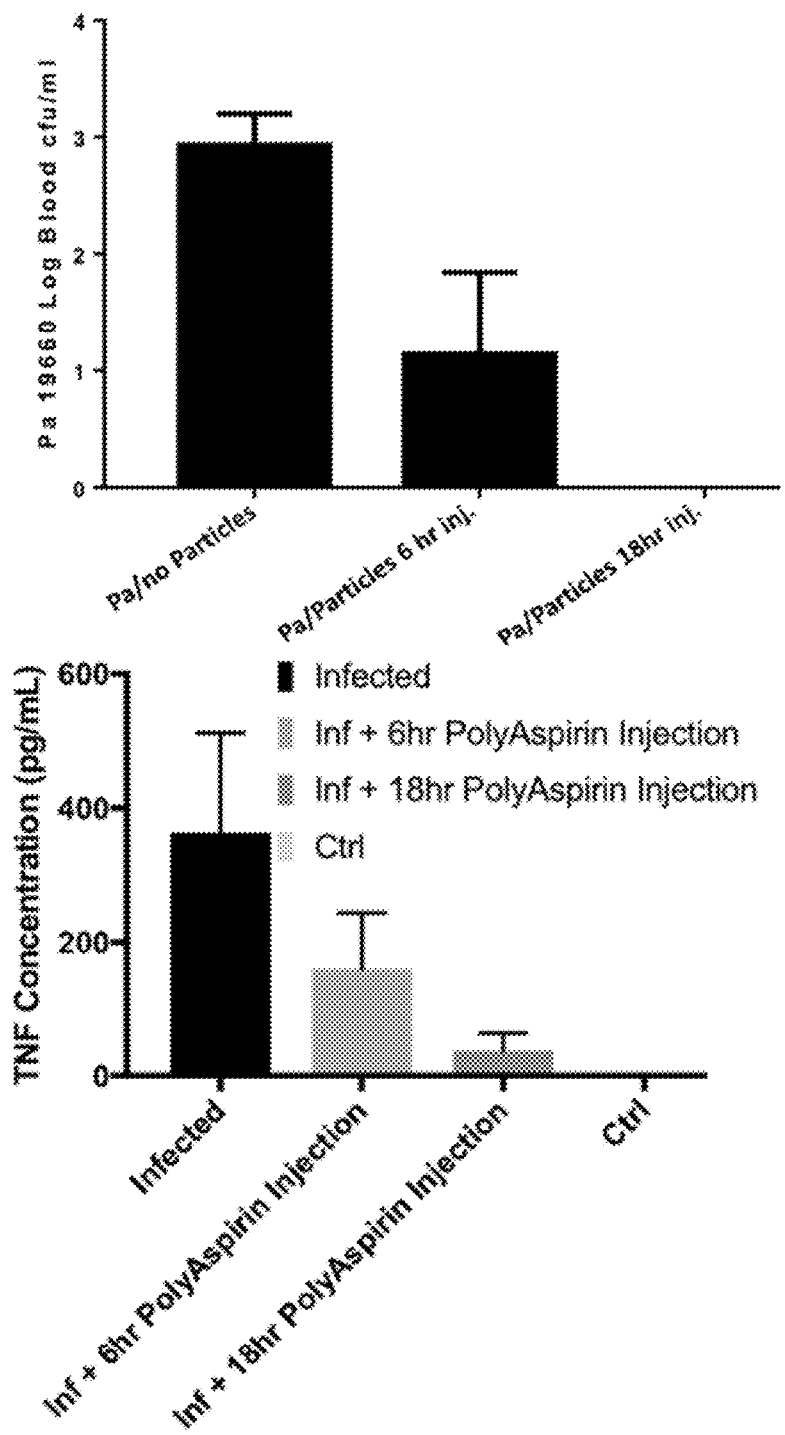
FIG. 4: Shows bacterial counts in the blood (top), and TNF-α concentrations in the BALF of P. aeruginosa infected mice (C57BL/6J) with no microparticles (MPs), or with Poly-A MPs 6 hrs or 18 hrs after infection.
Figure 5:
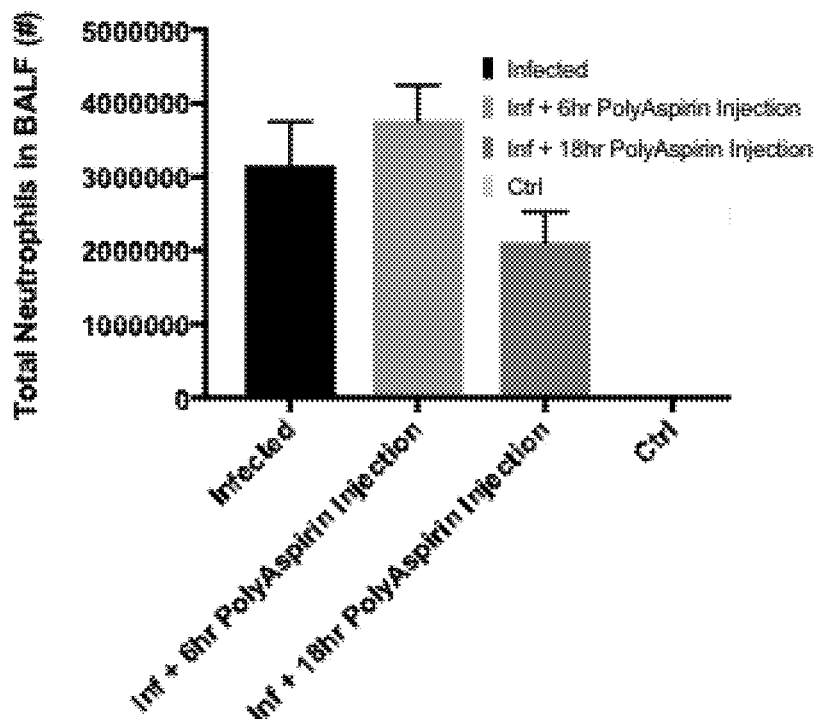
FIG. 5: Shows neutrophil counts in the BALF of P. aeruginosa (Pa) infected mice (C57BL/6J) without or with Poly-A microparticle (MP) treatment at 6 hrs and 18 hrs after bacterial infection. BALF samples were harvested 24 hrs after infection.

Example 2—Poly-A MPs do not Exacerbate Bacterial Infection in Mice with Bacteria-Induced ALI To determine whether Poly-A MPs have utility in the clinical setting of ALI/ARDS, i.e., whether Poly-A MP therapy functions without affecting a host's capacity to clear a primary infection, a mouse model of ALI/ARDS infected with *Pseudomonas* (*P.*) *aeruginosa* was investigated. Mice were infected with *P. aeruginosa* via intratracheal (i.t.) inoculation. *P. aeruginosa* bacteria grown in Difco broth were diluted to the desired concentration. Mice were anesthetized with ketamine and xylazine by the intraperitoneal route, the trachea exposed, and a 30 µl inoculum (7-8×10$^5$ CFU), or saline, were administered via a sterile 26-gauge needle. At either 6 hrs or 18 hrs after infection, Poly-A MPs were intravenously injected (IV; tail vein), and mice were euthanized at 24 hrs after infection. At 24 hrs after infection, the blood CFU was significantly lower in the Poly-A MP treated mice than in the untreated mice for both the 6 hrs and 18 hrs injection points (FIG. 4). Results in FIG. 5 show that the injection of Poly-A MPs at the 18 hrs interval reduced neutrophils in the lung BALF at the 24 hr sample collection. Conversely, the neutrophil count in the BALF for the Poly-A MP injection at the 6 hr interval was the same as for non-treated, infected mice. These data show that Poly-A MPs do not negatively impact a host's ability to clear a primary lung infection. In keeping with BALF neutrophil data, Poly-A MP treatment at the 18 hrs interval prevents the systemic dissemination of the infection, with no trace of *P. aeruginosa* found in blood at 24 hrs after infection. Lower concentrations of TNF-α (FIG. 4) IL-6, KC, and MCP-1 in the BALF with Poly-A MP treatment (FIG. 16) were observed Taken together, these data indicate that the timing of particle injection is important for efficacy in treating ALI. In view of the lower 24 hrs BALF neutrophil count for particle treatment at 18 hrs after infection vs. treatment at 6 hrs, a ramp-up interval after bacterial infection but before particles are injected may underly a therapeutic effect. Although the present invention is not confined to a specific mechanism or mechanisms, a minimum number of neutrophils may first enter lung tissue to facilitate bacteria clearance, but before extensive damage is done to the lungs. Thereafter, Poly-A MPs halt neutrophil lung transmigration, and mitigate injury while allowing natural host immunity or an active pharmaceutical ingredient (API) to clear the primary infection.

Example 3—Neutrophil-Poly-A MP Interactions in LPS-Induced Lung Injury Models

Methods

To determine whether Poly-A MP administration mitigates neutrophil infiltration into the lungs in a murine model of ALI, and to determine whether Poly-A MP particles have therapeutic advantages compared to polystyrene (PS) particles and vehicle controls, an LPS-induced model of ALI was used, and the total BALF cells, % of BALF neutrophils and macrophages, and inflammatory cytokine concentrations were quantified and compared.

Particle Degradation

Figure 10:
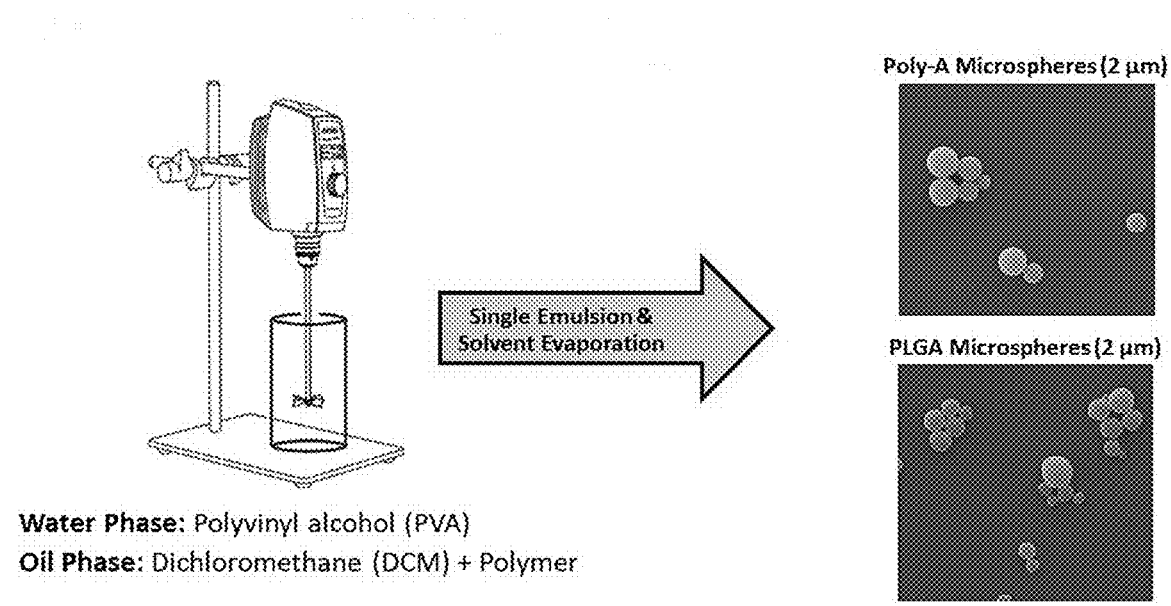
FIG. 10: Shows Poly(lactic-co-glycolic acid) (PLGA) and Poly-A microsphere particle fabrication using single emulsion and solvent evaporation.
Figure 11:
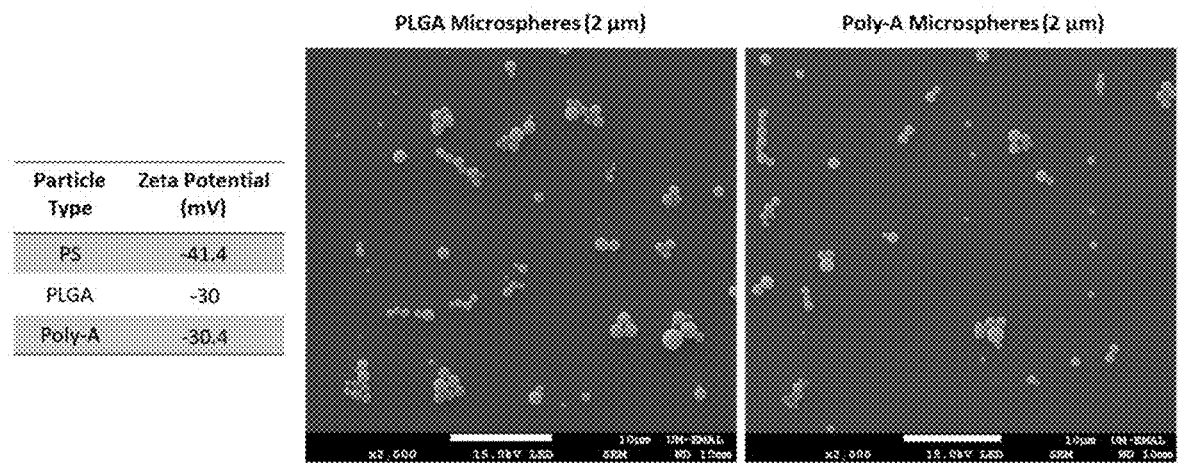
FIG. 11: Shows PLGA and Poly-A microspheres and Zeta-potentials (mV). The Zeta potential is a function of the surface charge of a particle relative to the nature of the medium that surrounds it. The value correlates to how particles will interact with WBCs. The Zeta potential value for Poly-A is similar to PLGA, but Poly-A has an added beneficial effect in ALI/ARDS.
Figure 12:
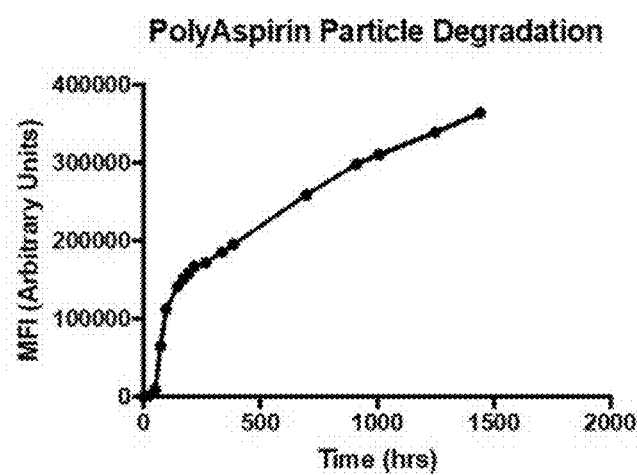
FIG. 12: Shows A) Poly-A particle degradation over time (hours), and B) concentration of released salicylic acid (SA) by incubating particles in plasma (Conc.=0.6 mg/mL).
Figure 12:
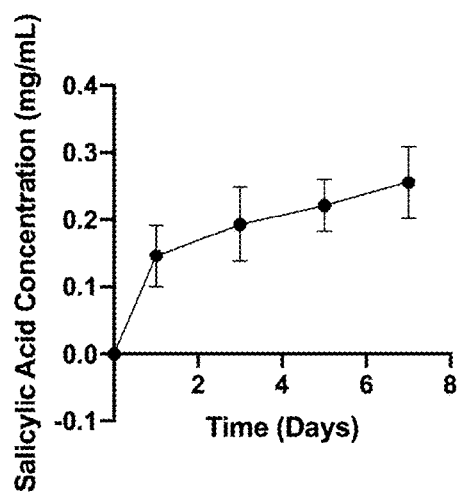
Figure 13:
FIG. 13: Shows injection timeline for a BALB/c model of lung inflammation after lipopolysaccharide (LPS) tracheal instillation. LPS inflames the lungs and gives rise to neutrophil infiltration. Two hours after particle administration, mice are euthanized and lungs are lavaged to collect cells in the airspaces. The supernatant is analyzed for the presence of inflammatory markers.

1×10$^7$ Poly-A nTP particles as determined by manual count on a hemocytometer were suspended in 10 mL of PBS –/– and placed under rotation at 37° C. (FIG. 10) The particles were centrifuged and the supernatant was serially removed and replaced. The supernatant was then added to a 96-well plate and the fluorescence intensity was measured (ex=315 nm and em=408 nm for salicylic acid). The cumulative fluorescence intensity at each timepoint is plotted versus degradation time in FIG. 12 (MFI=mean fluorescent intensity)

Acute Lung Injury (ALI) Model

Male BALB/c or C57BL/6J mice were anesthetized with inhaled isoflurane, and given 50 µL of 0.4 mg/mL LPS orotracheally to induce lung inflammation. Particles (2×10$^8$ in 100 µL PBS per mouse) were injected at either 2 hrs or 6 hrs post-instillation via tail vein catheter. Methods of euthanasia and sample processing are shared with the P. Aeruginosa model (below) except instead of cytospin BALF, cells were stained with CD45, CD11b, and Ly6G, and were fixed overnight before flow cytometry to determine the % of neutrophils and macrophages in each sample.

Results

Figure 14:
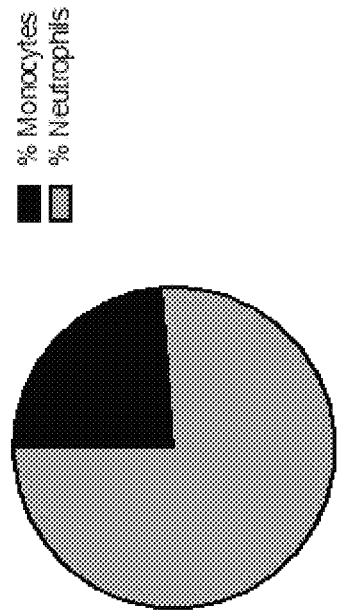
FIG. 14: Shows BALF percent of monocytes and neutrophils without LPS injury, percent of monocytes and neutrophils after LPS injury and no treatment, percents of monocytes and neutrophils after LPS injury and treatment with Poly-A particles, and total BALF cell counts in untreated, LPS injury only, and LPS injury/Poly-A particle treatment. BALB/c mice were induced to have ALI via instillation of LPS in the lungs. Untreated mice received no LPS. Data shown in "Untreated Monocytes vs. Neutrophils" are from mice that received no LPS and no particle treatment. Data shown in "LPS Monocytes vs. Neutrophils" are from mice that received LPS and no particle treatment. Neutrophils predominate in the BALF. Data shown in "LPS+P Monocytes vs. Neutrophils" are from mice that were administered LPS, and then Poly-A particle treatment at 1 hr after LPS. The number of neutrophils in the lungs is reduced significantly. The bar graph provides total cell counts.
Figure 14:
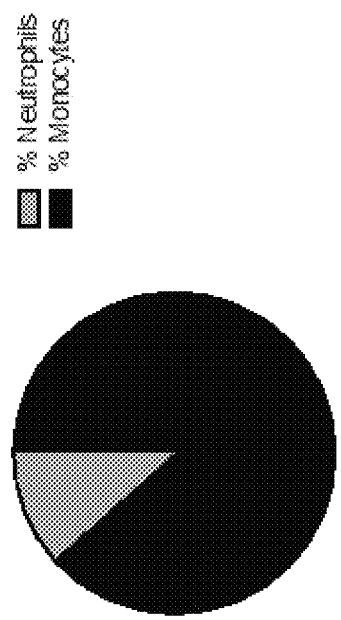
Figure 14:
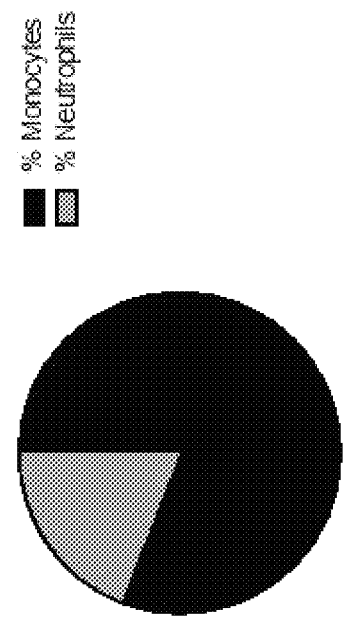
Figure 14:
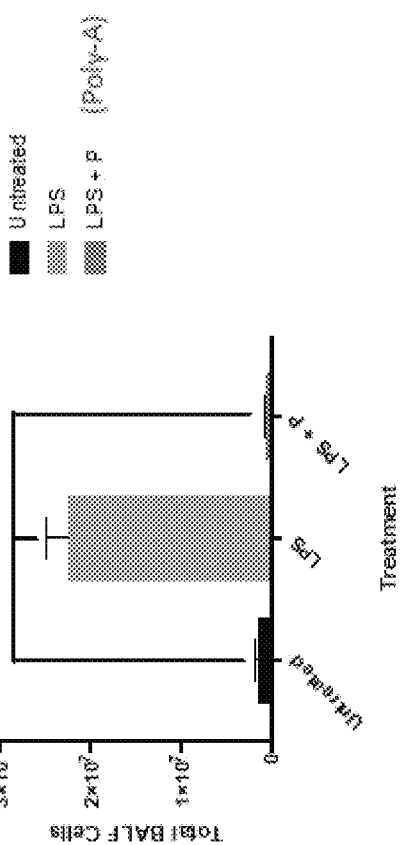
Figure 15:
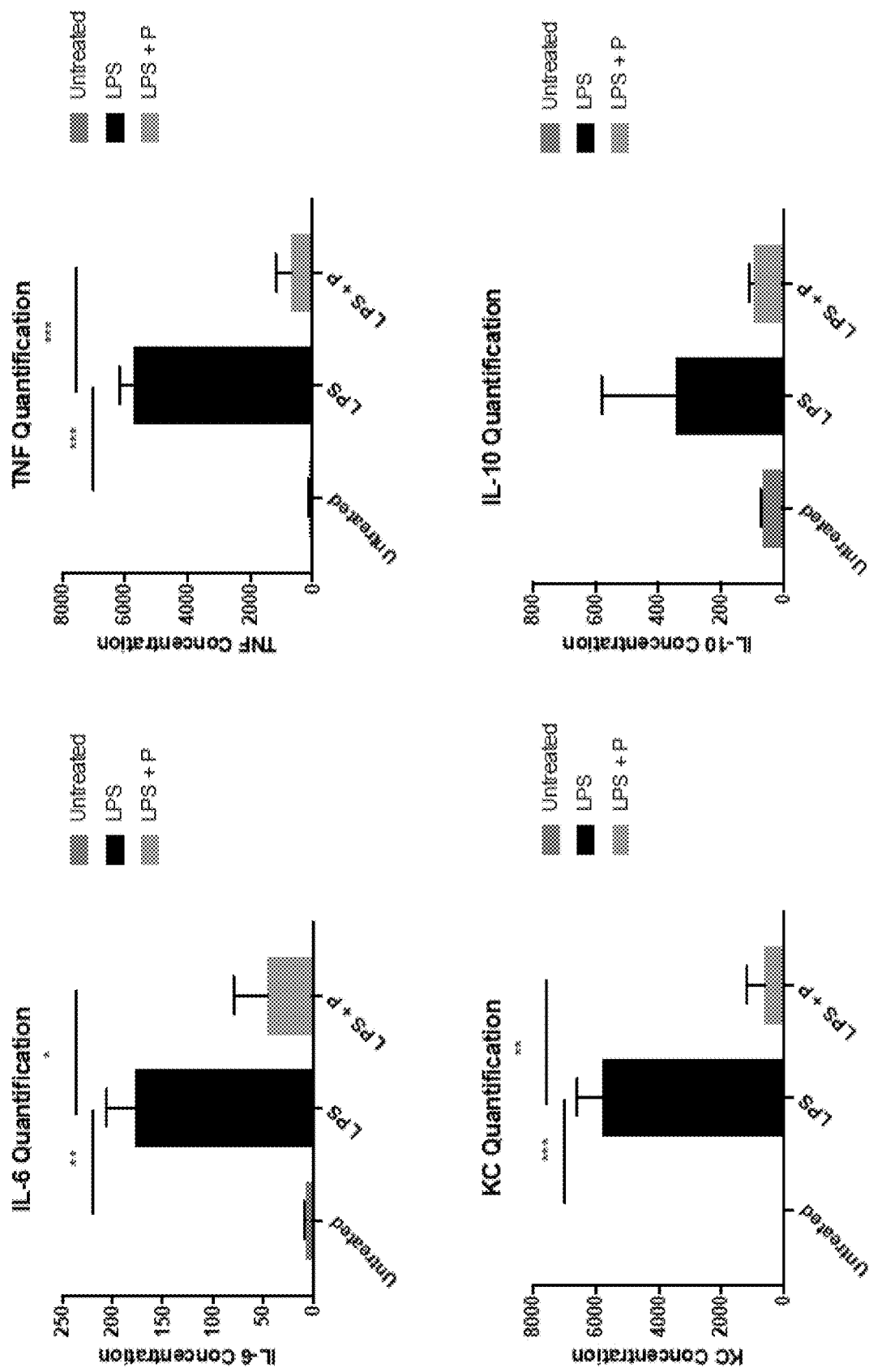
FIG. 15: Shows comparative IL-6, TNF-α, KC and IL-10 concentrations in uninjured/untreated mice, in LPS injured/untreated mice, and in LPS injured/Poly-A particle treated mice (LPS+P).
Figure 16:
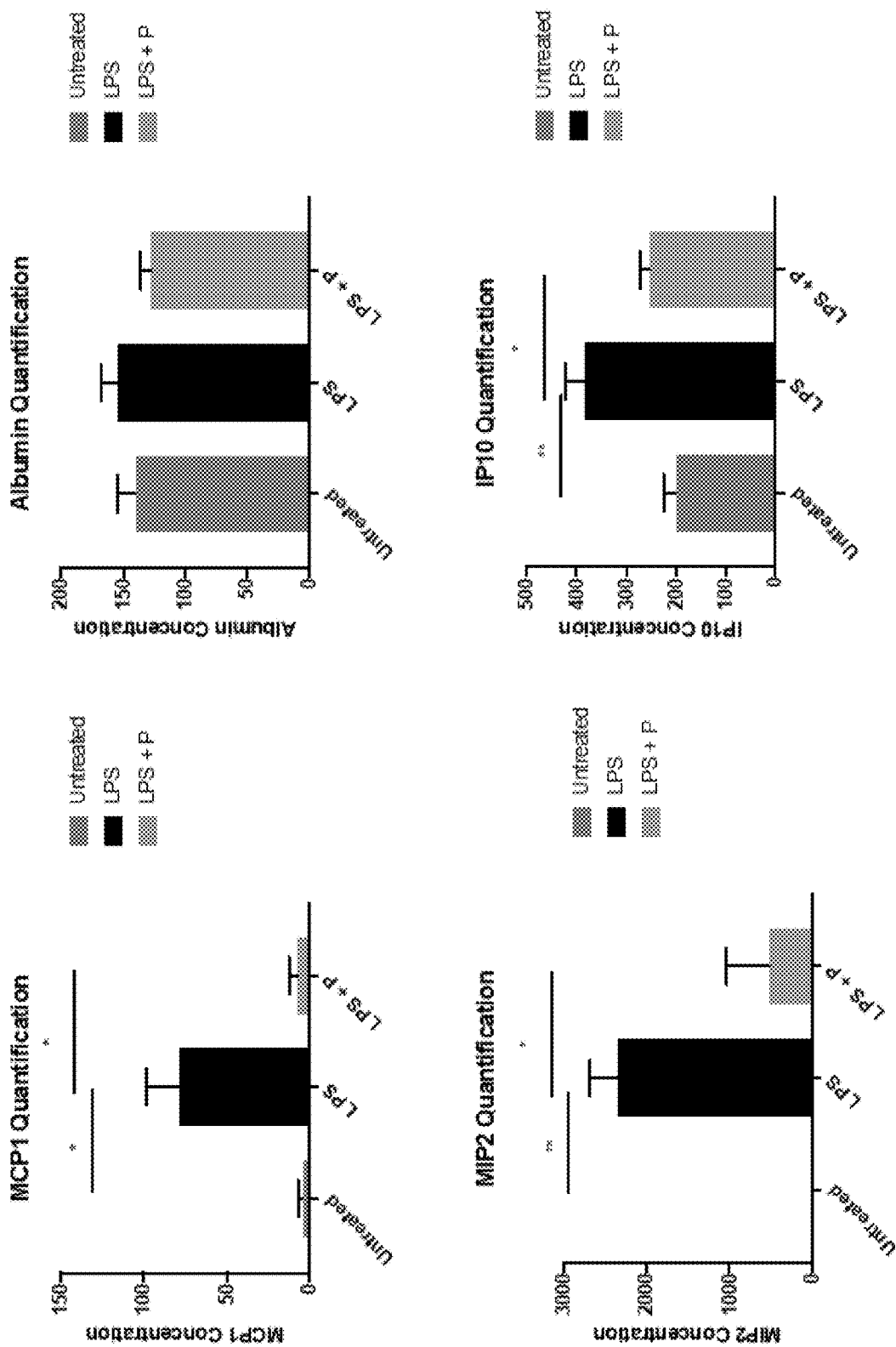
FIG. 16: Shows comparative MCP-1, albumin, MIP2 and IP10 concentrations in uninjured/untreated mice, in LPS injured/untreated mice, and in LPS injured/Poly-A particle treated mice.
Figure 17:
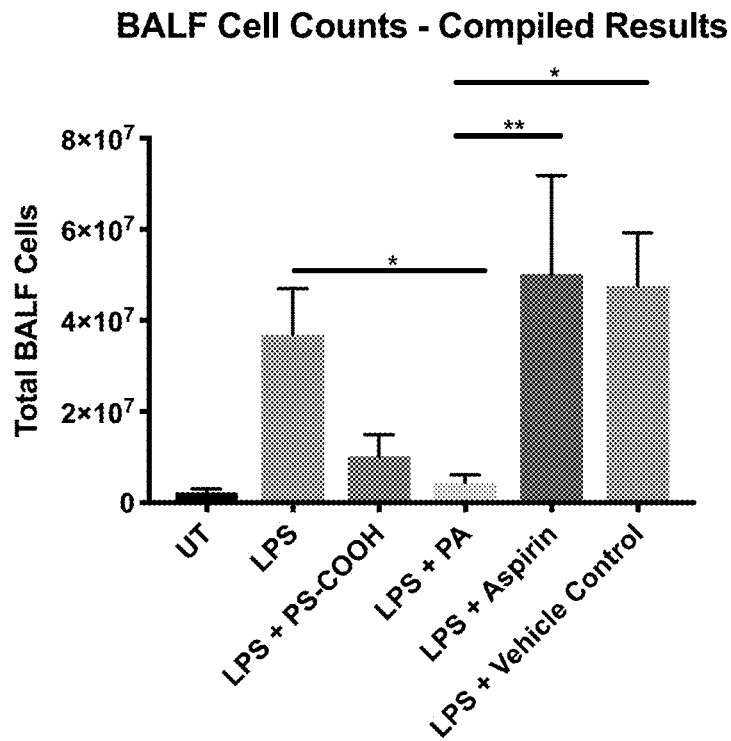
FIG. 17: Shows cell counts in BALF samples from untreated BALB/c mice, LPS injured BALB/c mice, LPS injured/PS—COOH particle treated BALB/c mice, LPS injured/Poly-A particle treated BALB/c mice, LPS injured/aspirin treated BALB/c mice, and LPS injured/vehicle control treated BALB/c mice averaged over multiple experiments. Poly-A particles provide protection from lung injury. (PA=Poly-A.)
Figure 18:
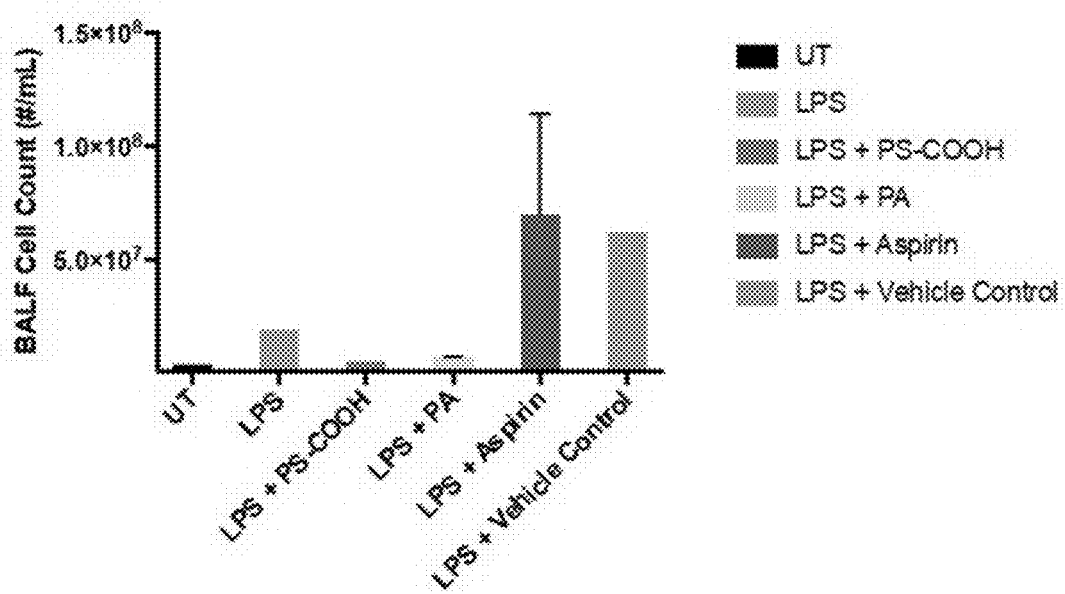
FIG. 18: Shows cell counts in BALF samples from untreated mice, LPS injured mice, LPS injured/PS—COOH particle treated mice, LPS injured/Poly-A particle treated mice, LPS injured/aspirin treated mice, and LPS injured/vehicle control treated mice in a single experiment.
Figure 19:
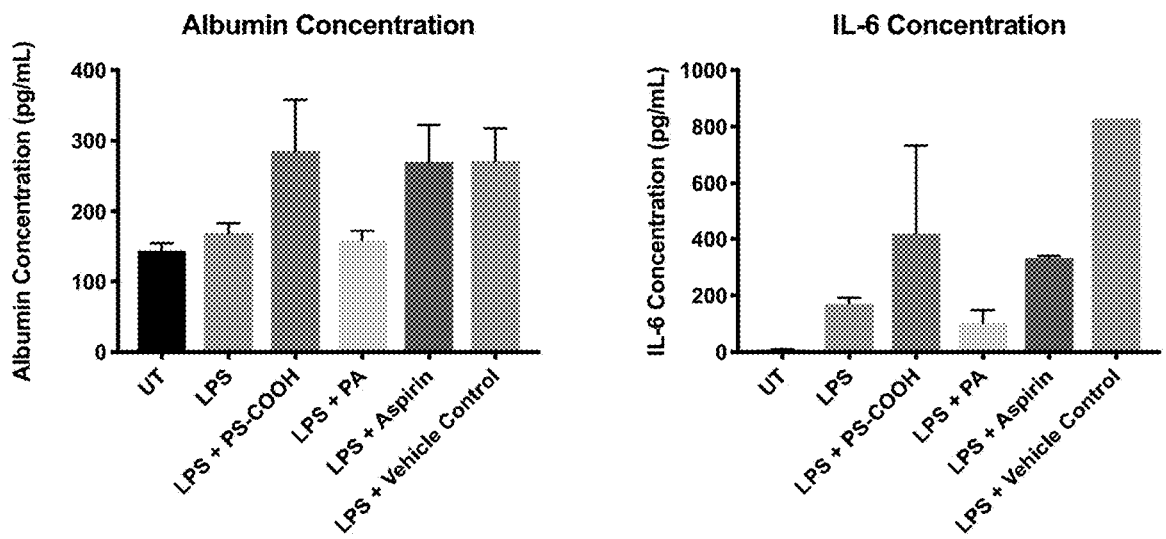
FIG. 19: Shows albumin concentrations and IL-6 concentrations in BALF supernatants from untreated mice, LPS injured mice, LPS injures/polystyrene (PS—COOH) particle treated mice, LPS injured/Poly-A particle treated mice, LPS injured/aspirin treated mice, and LPS injured/vehicle control treated mice.
Figure 20:
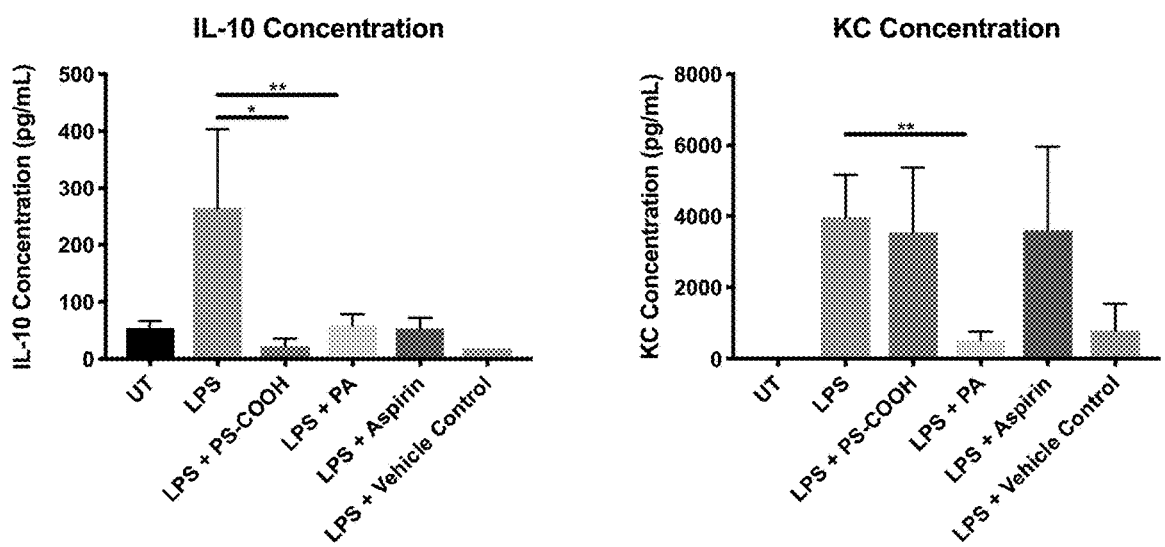
FIG. 20: Shows IL-10 and KC concentrations in BALF supernatants from untreated mice, LPS injured mice, LPS injured/polystyrene (PS—COOH) particle treated mice, LPS injured/Poly-A particle treated mice, LPS injured/aspirin treated mice, and LPS injured/vehicle control treated mice.
Figure 21:
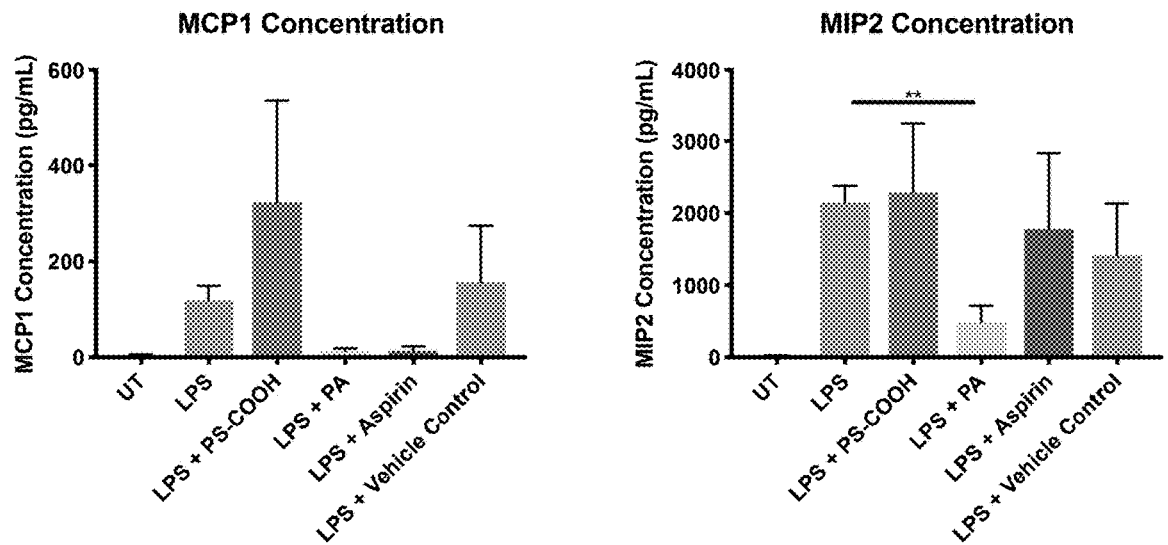
FIG. 21: Shows MCP1 and MIP2 concentrations in BALF supernatants from untreated mice, LPS injured mice, LPS injured/polystyrene (PS—COOH) particle treated mice, LPS injured, Poly-A particle treated mice, LPS injured/aspirin treated mice, and LPS injured/vehicle control treated mice.
Figure 22:
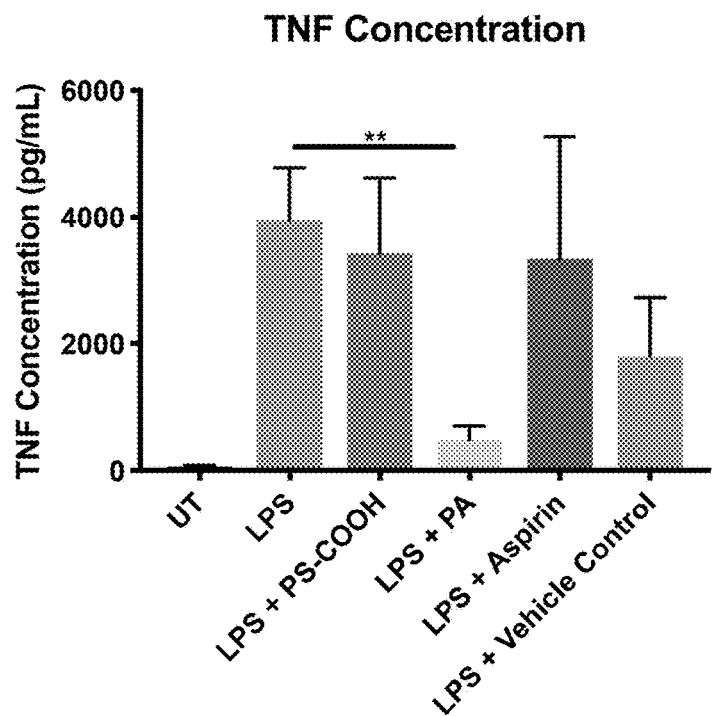
FIG. 22: Shows TNF-α concentrations in BALF supernatants from untreated mice, LPS injured mice, LPS injured/polystyrene (PS—COOH) particle treated mice, LPS injured/Poly-A particle treated mice, LPS injured/aspirin treated mice, and LPS injured/vehicle control treated mice.

Poly-A nTP administration reduces neutrophil infiltration and the concentration of inflammatory cytokines in the lungs after LPS, denoting mitigation of neutrophil mediated inflammatory responses. (FIGS. 14, 15, and 16.) Both PS and Poly-A nTPs reduce neutrophil infiltration into the lungs after LPS, but only Poly-A MP reduces the concentration of inflammatory cytokines in the lungs. (FIGS. 17, 18, 19, 20, 21, and 22.)

Example 4—Optimal Administration Intervals

Figure 23:
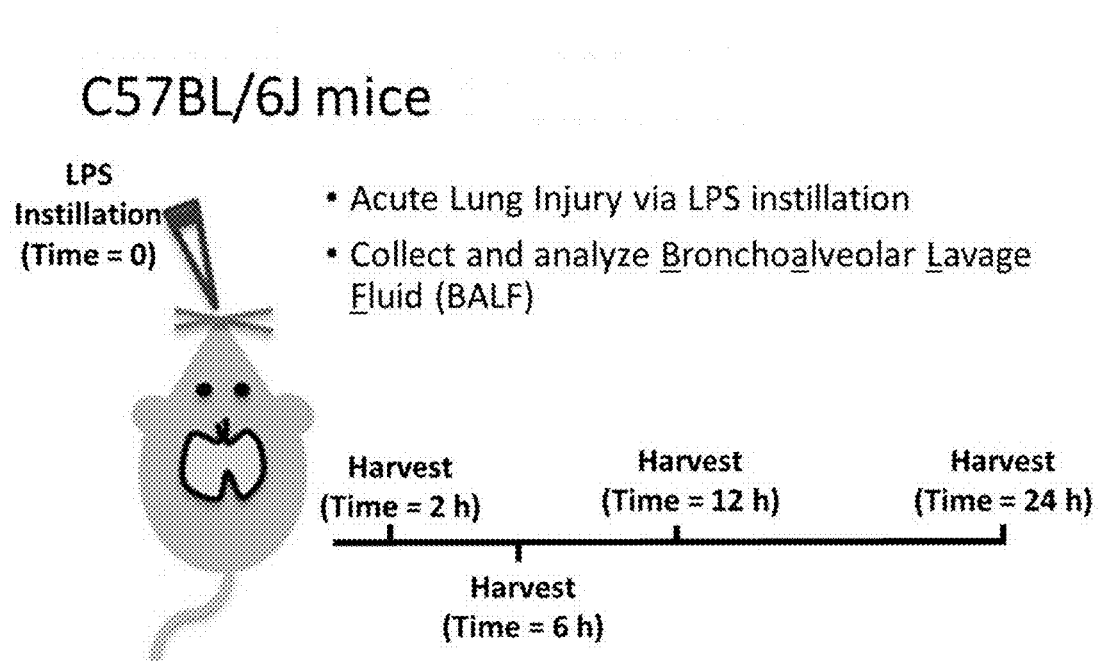
FIG. 23: Shows a representative experimental timeline for collection of BALF samples after ALI caused by LPS instillation in C57BL/6J mice without particle treatment.
Figure 24:
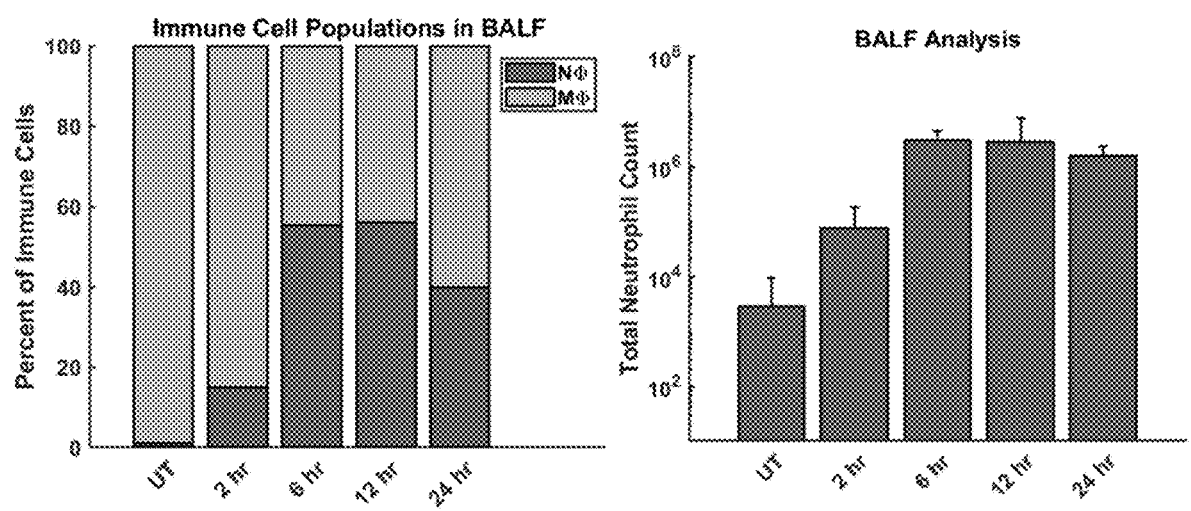
FIG. 24: Shows comparative intervals for neutrophil infiltration in the BALF after LPS injury (ALI) vs. percent of immune cells and total neutrophil counts in blood in sepsis for C57BL/6J.
Figure 25:
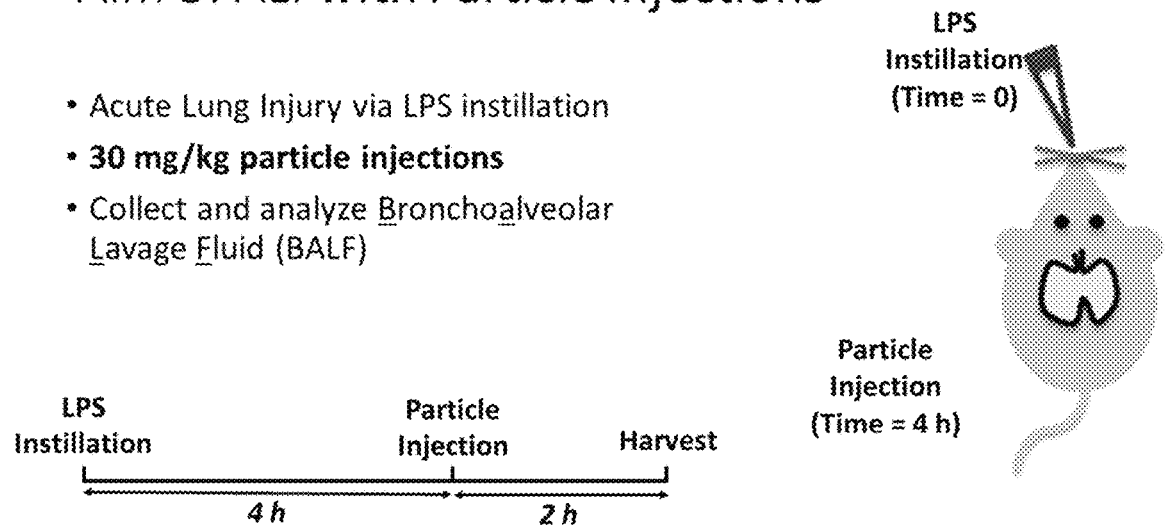
FIG. 25: Shows a representative experimental timeline for collection of BALF samples after ALI caused by LPS instillation using 30 mg/kg injections of Poly-A particles.
Figure 26:
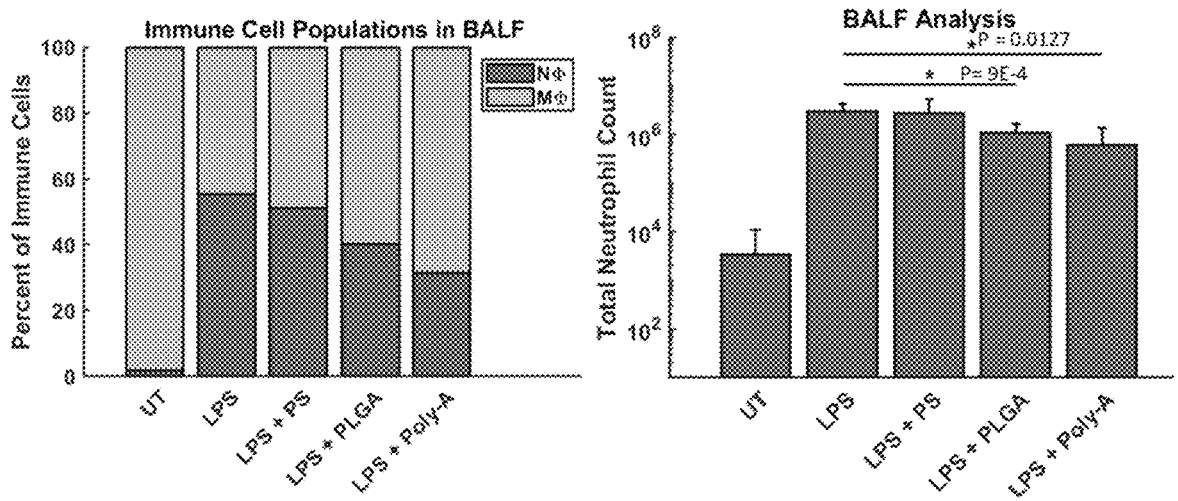
FIG. 26: Shows the comparative impacts of Poly-A particle administration at 4 hrs after LPS on changes in the percent of immune cells and total neutrophil counts in BALF samples relative to treatments with LPS only, LPS plus Polystyrene (PS) particles, LPS plus PLGA particles, and LPS plus Poly-A particles.
Figure 27:
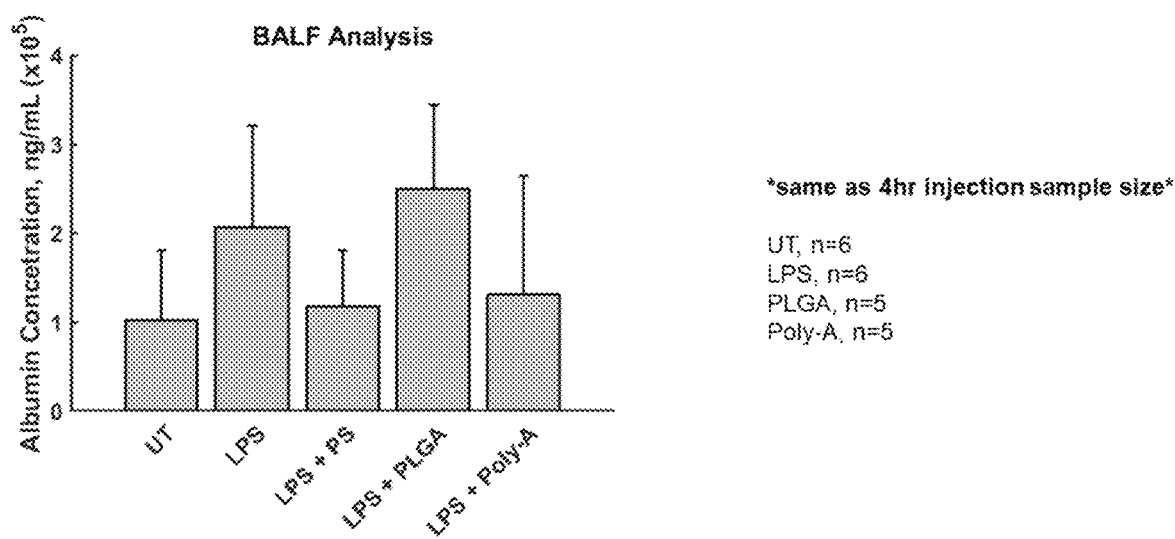
FIG. 27: Shows that Poly-A particles reduce albumin concentrations in BALF samples in LPS injured/PS particle treated mice, and in LPS injured/Poly-A particle treated mice similar to uninjured, untreated mice compared to LPS injured/untreated mice, and LPS injured/PLGA particle treated mice when treatment is provided 4 hrs after LPS injury. PLGA particles increase lung leakiness, whereas Poly-A particles protect the lungs from LTP injury as reflected in lower BALF albumin concentrations.
Figure 28:
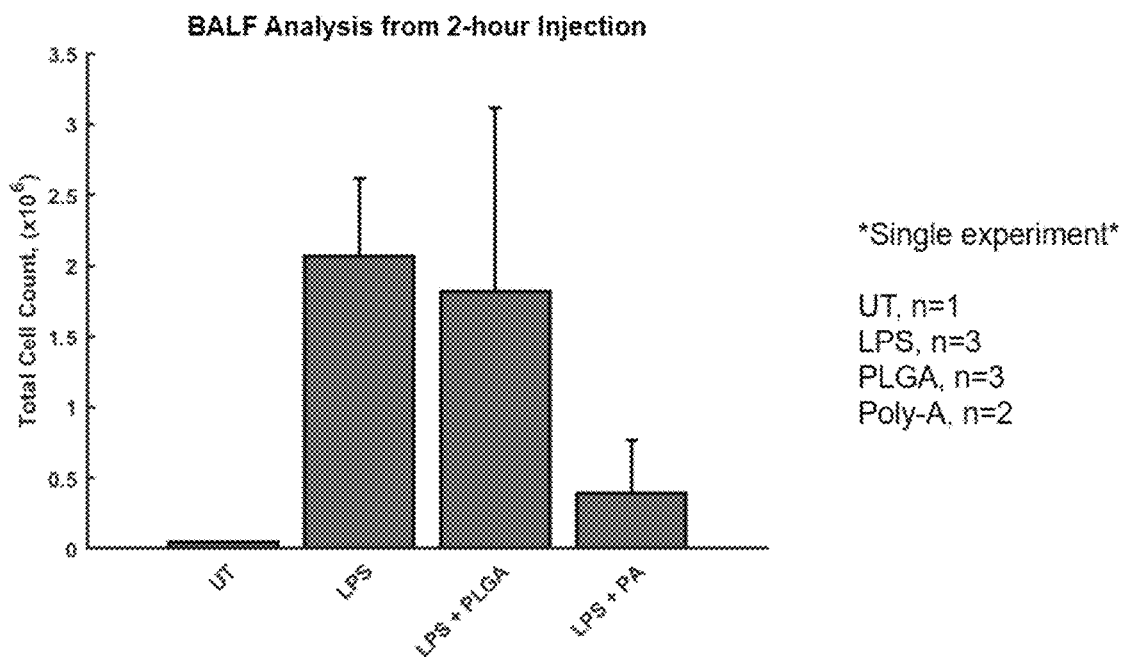
FIG. 28: Shows that the total cell count in BALF samples are highest in LPS injured/untreated mice and in LPS injured/PLGA particle treated C57BL/6J mice compared to LPS injured/Poly-A particle treated mice when treatment is provided 2 hrs after LPS injury. PLGA particles have no benefit on total BALF cell counts, whereas Poly-A particles protect the lungs from cellular infiltration when given 2 hrs after infection.
Figure 29:
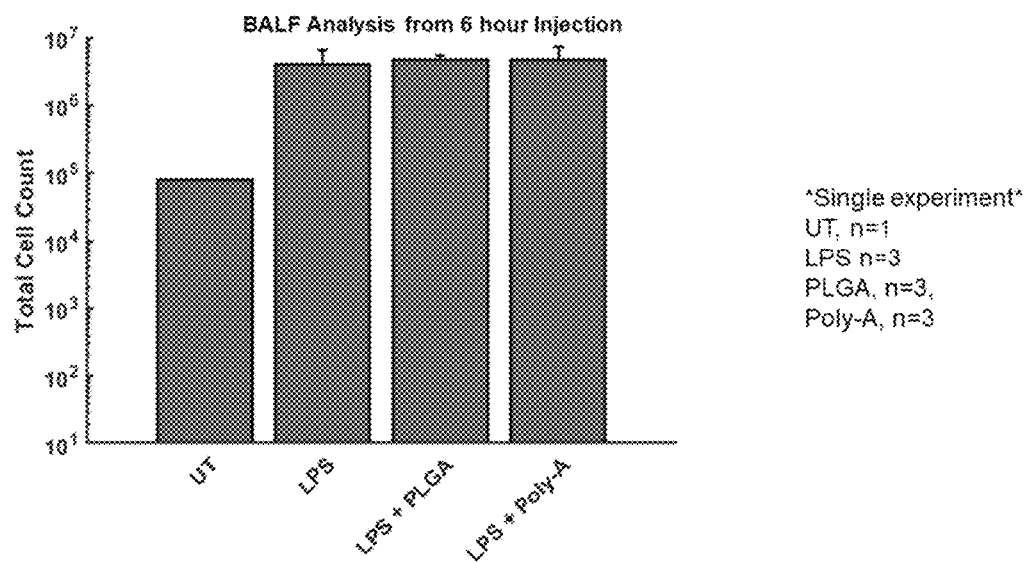
FIG. 29: Shows that there is no difference in treatment of LPS injured mice between no treatment, treatment with PLGA particles, and treatment with Poly-A particles when treatment is provided 6 hrs after LPS injury in C57BL/6J mice.

To characterize the timeline of neutrophil influx into the lungs, and to identify the optimal injection interval after infection for maximum therapeutic benefit, a model of intratracheal LPS administration in C57BL/6J mice was used for analysis of BALF samples. (FIG. 23). Influx of neutrophils into the alveolar space is greatest between 2 hrs and 6 hrs post-instillation. A 2 hr post-instillation Poly-A MP administration interval confers maximum reduction in neutrophil infiltration in animals under these conditions. (FIGS. 24, 25, 26, 27, 28 and 29.) (Neutrophil N Φ. and Macrophage M Φ.)

Example 5—Therapeutic Benefit of Poly-A MP Administration

The therapeutic benefits of Poly-A MP administration were identified using a bacterial model of ALI/ARDS in which mice were infected with *P. aeruginosa*, and Poly-A MPs were parenterally administered at 6 and 18 hours after infection.

Methods

Particle Preparation

Poly-A particles were prepared using a single emulsion solvent evaporation (ESE) method. 20 mg of Poly-A polymer were dissolved in 20 mL of dichloromethane. Then, 75 mL of 1% polyvinyl alcohol (PVA) solution was placed on a mixer at 4250 rpm. Poly-A solution was slowly injected into the PVA solution, and allowed to mix for 2 hrs. After mixing, the solution was allowed to settle for ~45 minutes, and the particles were removed and washed by centrifugation 3× with DI water. Particles were then lyophilized and stored at −40° C. until use. Particle size was determined by scanning electron microscopy (SEM) and dynamic light scattering (DLS) and particle concentration was determined via counting on a hemocytometer.

Bacterial Growth

*P. aeruginosa* cultures were grown overnight in Difco nutrient broth at 37° C. under constant shaking. The concentration of bacteria in the broth was determined by measuring light absorbance at 600 nm, then plotting the optical density (OD) on a standard curve generated by known colony forming units (CFUs)

Intranasal Bacterial Inoculation

Figure 30:
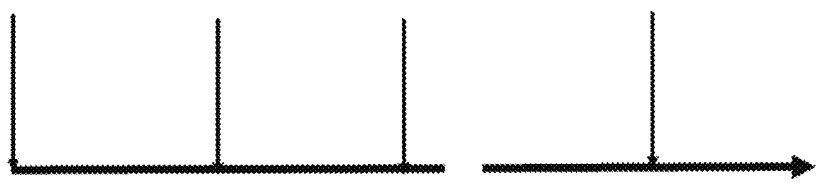
FIG. 30: Shows a representative experimental timeline for mice P. aeruginosa infection, Poly-A particle administration, and collection of samples for BALF assays and blood colony forming unit (CFU) counts.

Mice were anesthetized with an intraperitoneal injection of ketamine/xylazine mixture, and given 30 µL of bacteria solution (15 µL in each nostril) intranasally to induce lung infection. (FIG. 30.)

Poly-A VTP Injection

At 6 hrs or 19 hrs post-infection, mice were placed in a restrainer, and a catheter was inserted into the tail vein. Each mouse received $2\times10^8$ particles in 100 µL of injection volume, for a dose of approximately 30 mg/kg. (FIG. 30.)

Euthanasia and Sample Processing 24 hours post-infection, mice were euthanized via $CO_2$ overdose. After euthanasia, the chest cavity was exposed and a cardiac puncture was used to collect blood. The trachea was exposed and opened, and the lungs were lavaged with 3 mL of PBS −/− to remove cells in the alveolar space. BALF samples were centrifuged and supernatants were stored at −80° C. for ELISA to quantify inflammatory cytokines. The cell pellets were resuspended in 500 µL of RPMI media, and aliquots were diluted 1:1 with Turk Blood Diluting Fluid and counted via hemacytometer. Cytospin samples were prepared and cells were stained to differentiate neutrophils from mononuclear cells. Blood and BALF samples were plated on agar plates and allowed to grow overnight at 37° C. to determine CFUs. Blood was centrifuged and plasma samples were collected and stored at −80° ° C. for ELISA analysis.

Results

Figure 31:
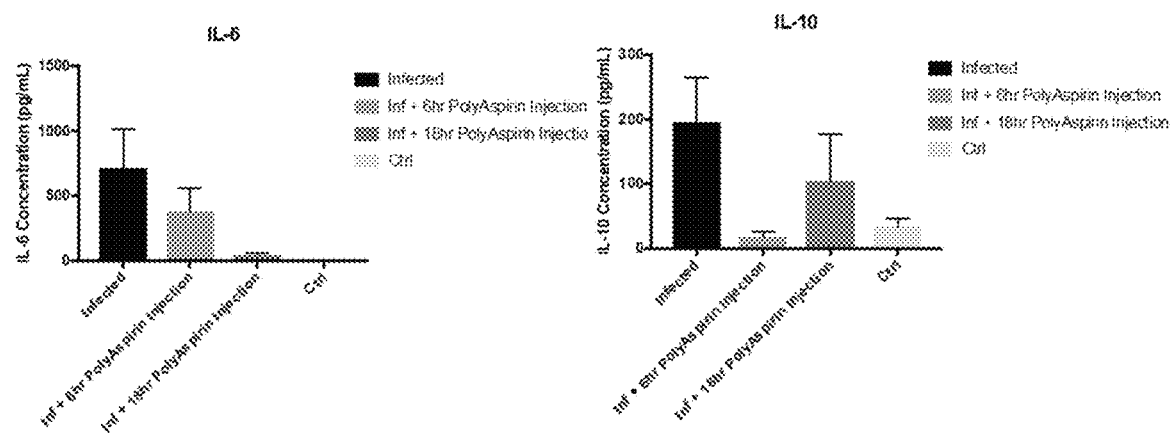
FIG. 31: Shows IL-6 and IL-10 comparative concentrations in mice infected with P. aeruginosa without Poly-A particle administration, with Poly-A particle administration at 6 hrs after infection, and at 18 hrs after infection, and in no infection control mice. Markers of inflammation are reduced with treatment with Poly-A particles, with greater benefit when particles are administered at 18 hours after infection.
Figure 32:
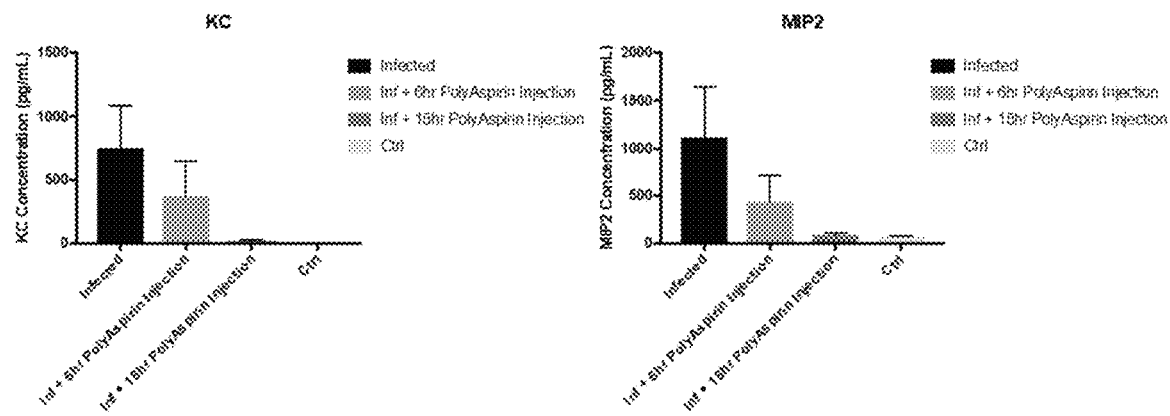
FIG. 32: Shows KC and MIP2 comparative concentrations in mice infected with P. aeruginosa without Poly-A particle administration, with Poly-A particle administration at 6 hrs after infection, and at 18 hrs after infection, and in no infection control mice. Markers of inflammation are reduced with treatment with Poly-A particles, with greater benefit when particles are administered at 18 hrs after infection.
Figure 33:
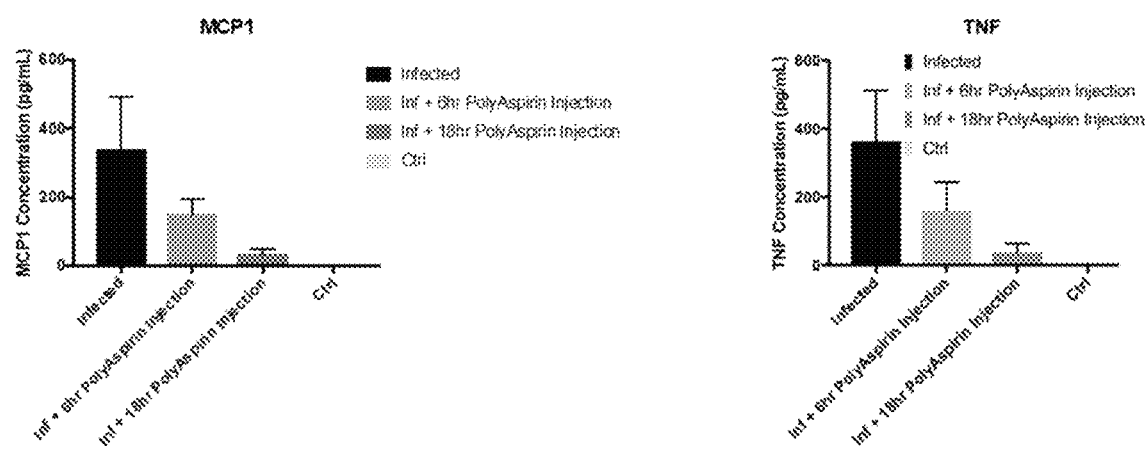
FIG. 33: Shows MCP-1 and TNF-α comparative concentrations in mice infected with P. aeruginosa without Poly-A particle administration, with Poly-A particle administration at 6 hrs after infection, and 18 hrs after infection, and in no infection control mice. Markers of inflammation are reduced with treatment with Poly-A particles, with greater benefit when particles are administered at 18 hours after infection.
Figure 34:
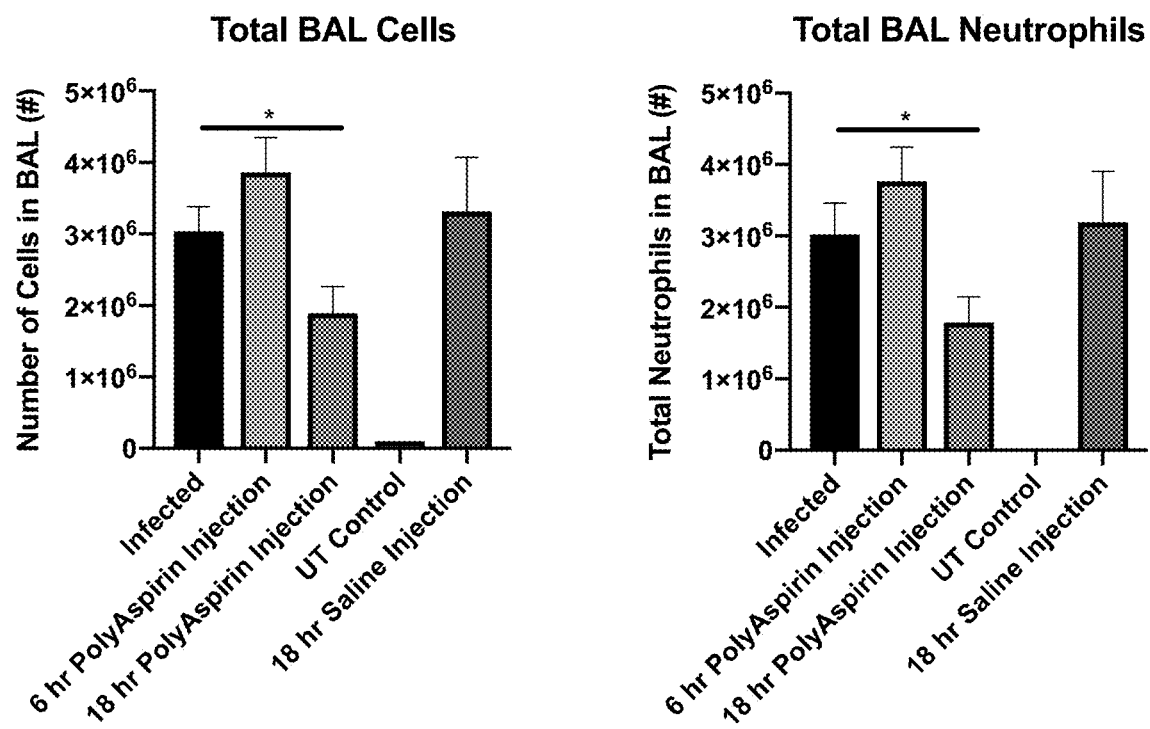
FIG. 34: Shows comparative total BALF cell counts and total BALF neutrophil counts in mice infected P. aeruginosa without Poly-A particle administration, with Poly-A particle administration at 6 hrs after infection, and 18 hrs after infection, and saline injection after 18 hrs after infection in no infection control mice. Treatment with Poly-A particles reduces the number of neutrophils with a greater reduction observed with administration at 18 hrs vs. 6 hrs after infection.

Poly-A MP administration at 6 hrs and 18 hrs reduced lung concentrations of IL-6, IL-10, KC, MIP2, MCP1, and TNF-α cytokines relative to *P. aeruginosa* infected but untreated control mice, indicating reduced pulmonary inflammation after Poly-A VTP treatment. (FIGS. 31, 32, and 33.) Poly-A MP treatment at 18 hrs after infection significantly reduced the number of neutrophils in BALF, but administration 6 hrs after infection did not. (FIG. 34.) Poly-A MP treatment at 18 hrs after infection reduced bacterial CFU in blood indicating that treatment serves to confine infection to the lungs.

Example 6—Therapeutic Benefit of Poly-A MP Administration

To ensure that Poly-A MPs cause a reduction in bacterial CFU blood counts, the Methods of Example 5 were repeated with 18 hr Poly-A MP particle administration in parallel with a saline intravenous (IV) control. Poly-A MP administration, but not saline, reduced CFU in the blood relative to the infected controls, indicating that Poly-A MPs contain infection to the lungs, and prevent systemic spread of the infection.

Example 7—Time Course of Pulmonary Neutrophil Infiltration after Infection

Figure 35:
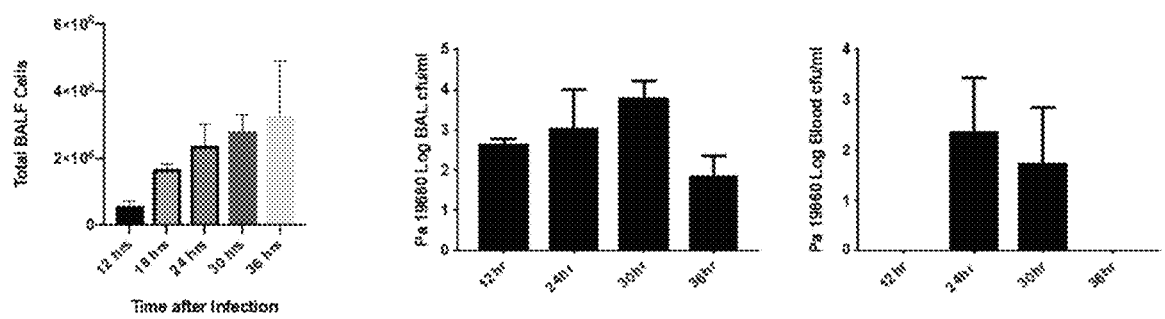
FIG. 35: Shows comparative total BALF cell counts, P. aeruginosa 19660 log BAL CFU/mL counts, and P. aeruginosa 19660 log blood CFU/mL counts at 12 hrs, 18 hrs, 24 hrs, 30 hrs and 36 hrs after P. aeruginosa infection and no treatment. White cells and bacteria increase in the lungs after infection, as do bacterial CFU counts in blood.
Figure 36:
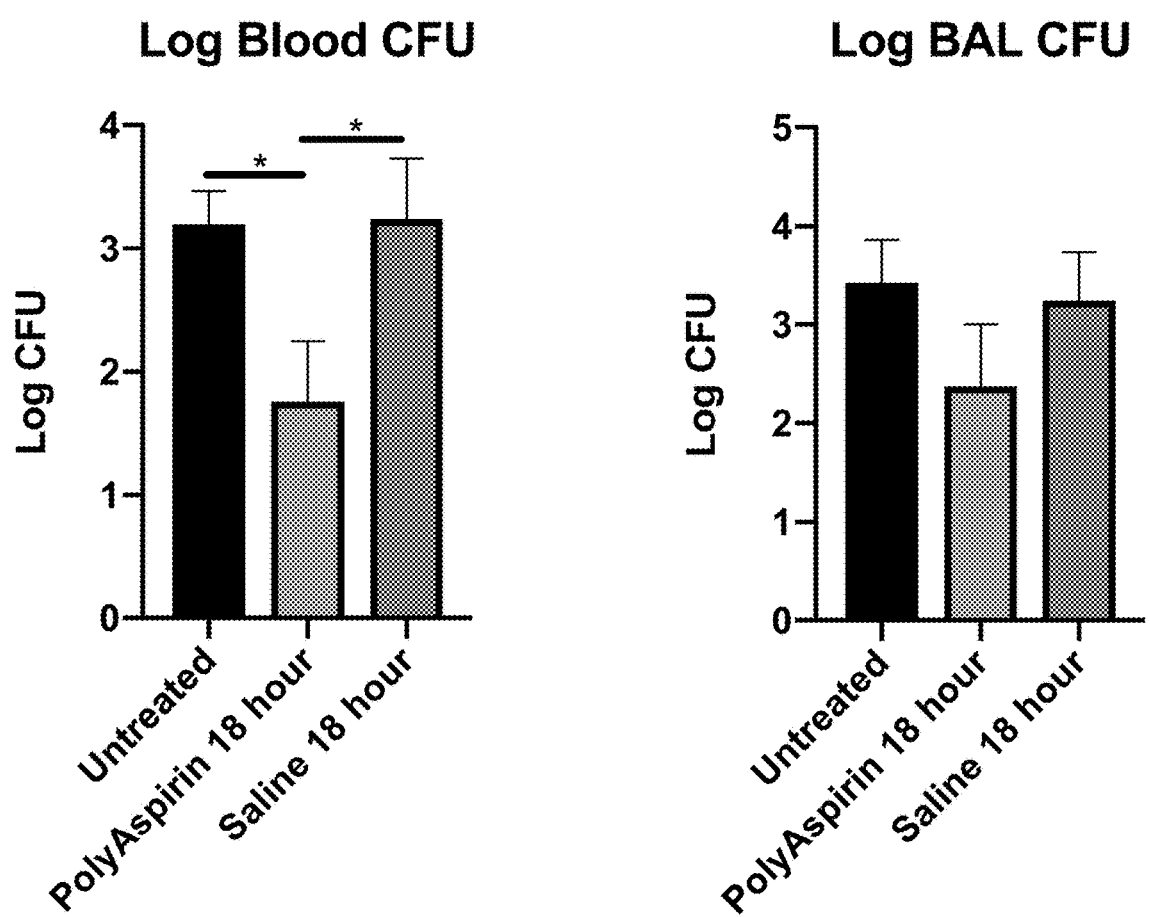
FIG. 36: Shows comparative P. aeruginosa 19660 log BAL CFU/mL counts, and P. aeruginosa 19660 log blood CFU/mL counts at 24 hrs after infection in untreated mice, in mice treated with intravenous Poly-A particles intravenously, and in mice treated with intravenous saline assayed at 18 hrs. Poly-A particles decrease P. aeruginosa 19660 log BAL CFU/mL counts, and *P. aeruginosa* 19660 log blood CFU/mL counts at 24 hrs after infection.

To determine the time course of neutrophil influx into the lungs after infection BALF cell counts, BALF *P. aeruginosa* 19660 counts, and blood *P. aeruginosa* 19660 counts at 12 hrs, 18 hrs, 24 hrs, 30 hrs and 36 hrs after infection were measured. A marked increase in BALF cells was observed between 12 and 24 hours, with an associated increase in both lung and blood *P. aeruginosa* CFU counts. (FIGS. 35 and 36.)

Example 8—Therapeutic Benefit of Poly-A MP on Survival after Infection

Figure 37:
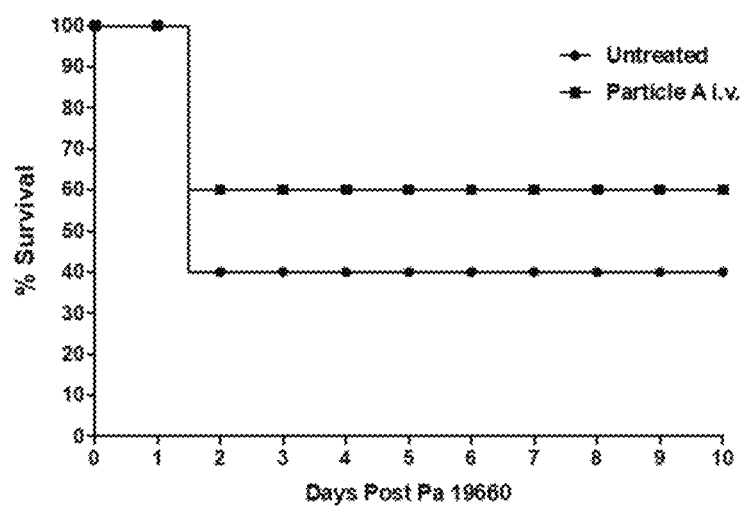
FIG. 37: Shows the comparative benefit of Poly-A particle treatment on daily survival to 10 days after *P. aeruginosa* infection. Mice were infected with *P. aeruginosa* and at 18 hrs after infection. A first subset was treated with Poly-A particles ("Particle A i.v."), and a second subset was untreated. Mice in the Poly-A treated subset had 60% survival compared to 40% survival in the untreated group.

To determine whether Poly-A MP particle administration has a positive impact on survival post-infection, mice were infected with *P. aeruginosa*, and half the mice were given Poly-A particles 18 hours post-infection. Poly-A MPs significantly reduced mortality in the infected mice. (FIG. 37.)

Example 9—Poly-A Particle Conjugation

Figure 38:
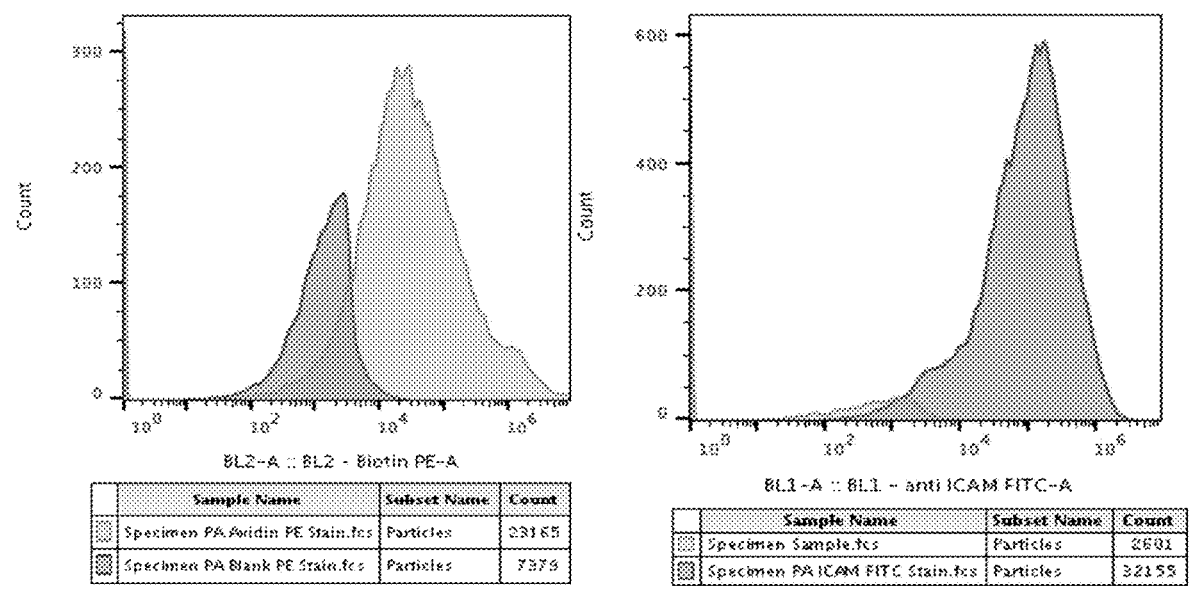
FIG. 38: Shows flow cytometry histogram plots of Poly-A-Avidin and Poly-A-anti-ICAM-1 VTP.
Figure 39:
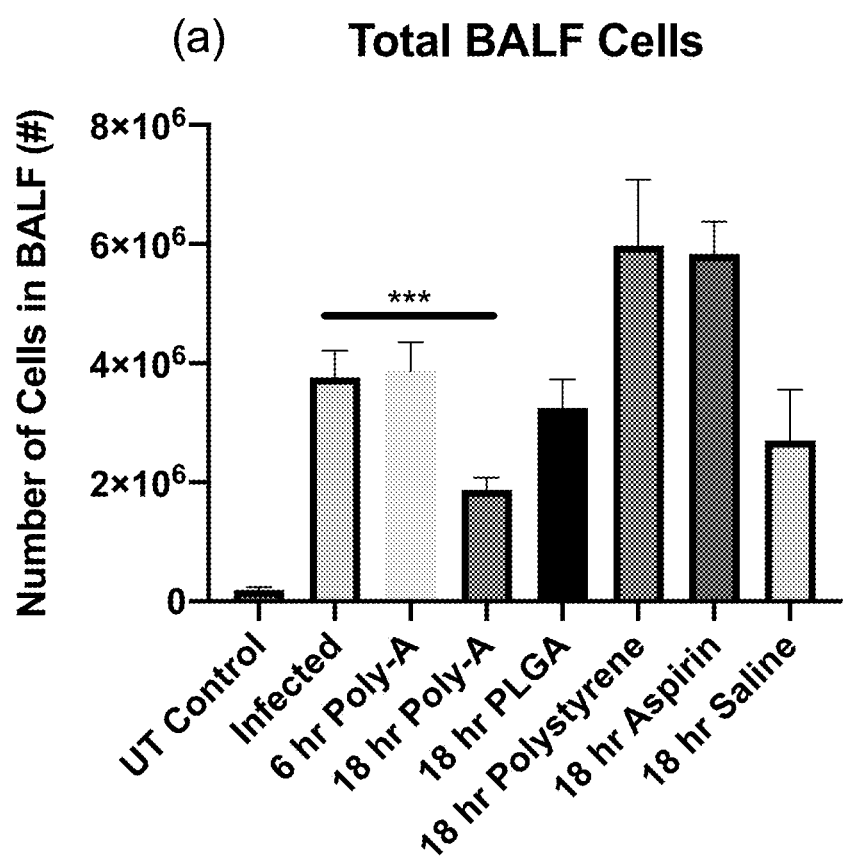
FIG. 39: Shows the impact of Poly-A particle injection on *P. aeruginosa* lung infection in C57BL/6J mice. Total cells in BALF at 24 hrs post-infection after 6 hr or 18 hr Poly-A injection, 18 hr PLGA injection, or 18 hr polystyrene injection are compared between infected mice and saline control.
Figure 40:
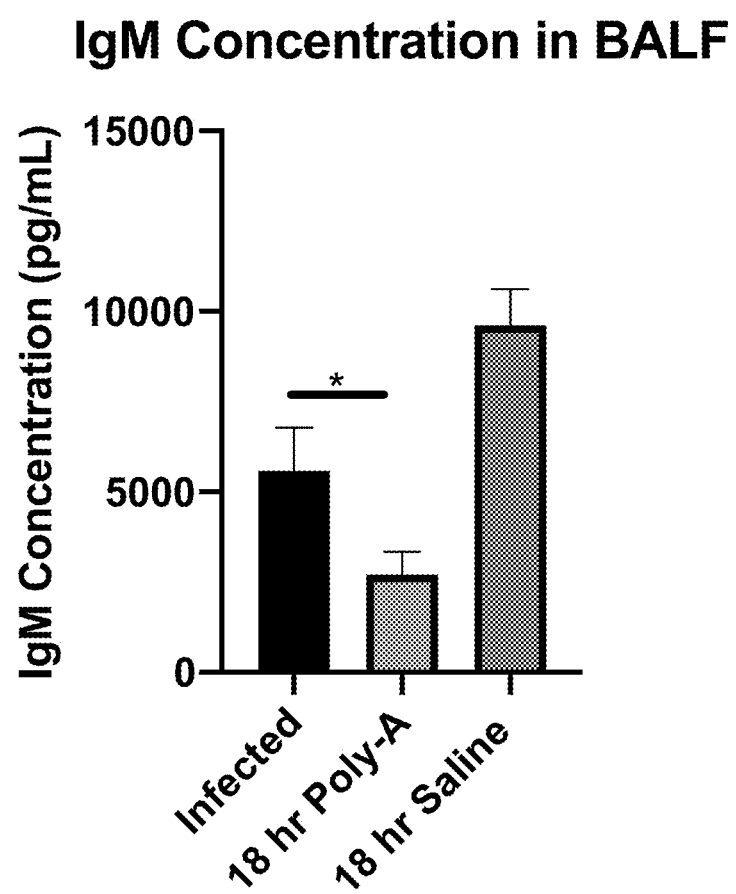
FIG. 40: Shows that the concentration of IgM in BALF is reduced infected mice by treatment with Poly-A particles.
Figure 41:
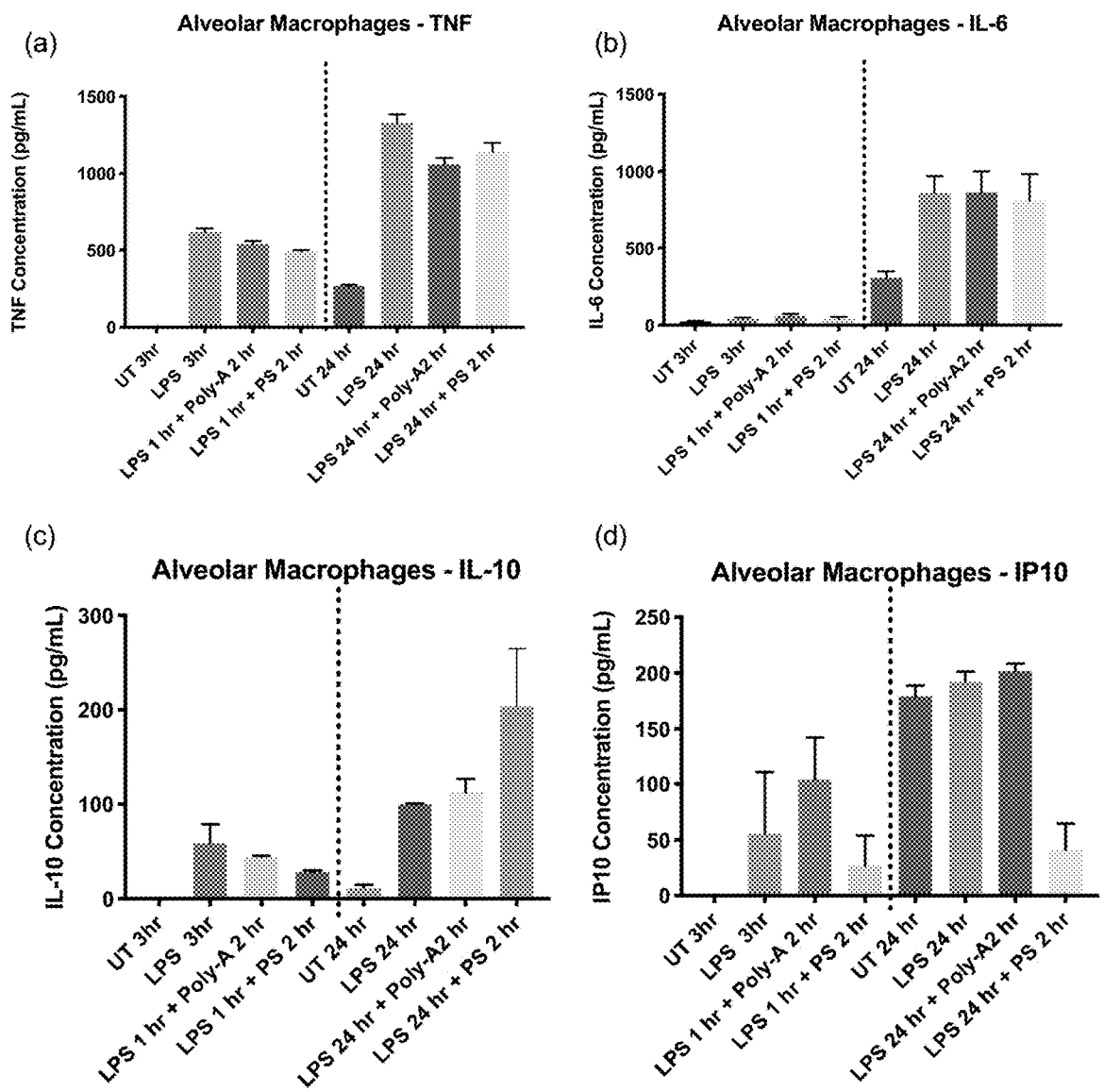
FIG. 41: Shows comparative concentrations of inflammatory cytokines by ELISA quantification of (a) TNF, (b) Il-6, (c) IL-10, and (d) IP-10 produced by alveolar macrophages in response to LPS treatment for 3 or 24 hours, with or without the addition of Poly-A or polystyrene (PS) particles.
Figure 42:
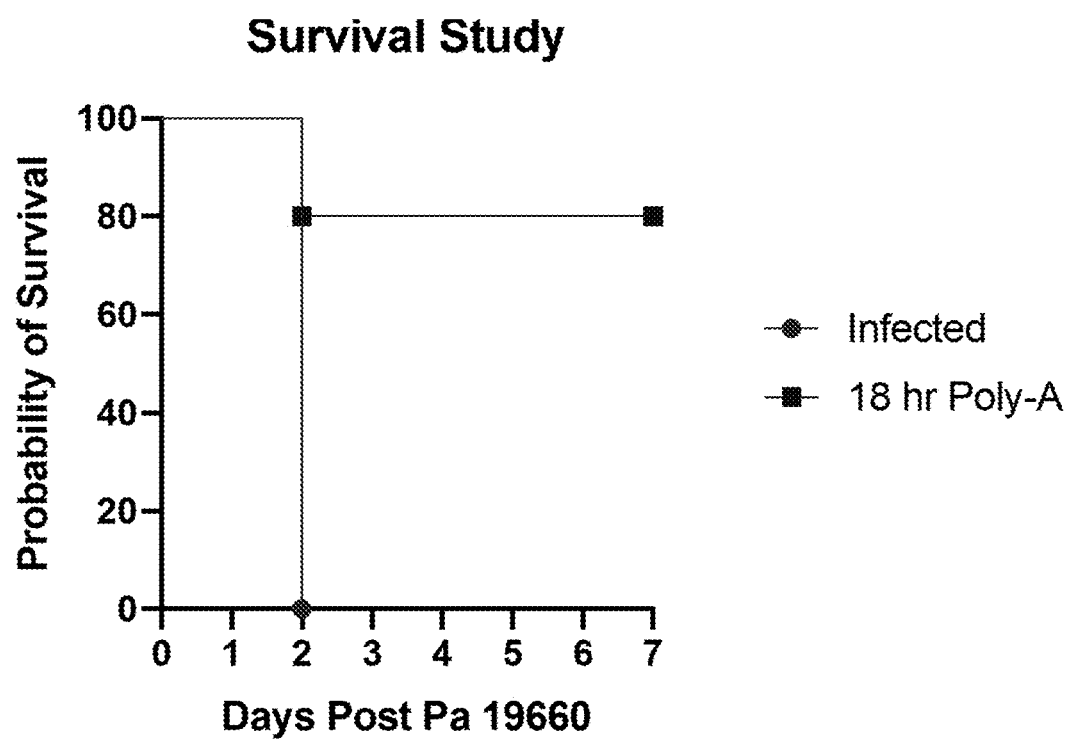
FIG. 42: Shows post-infection survival for *P. aeruginosa* infected mice (N=5 for each group) with and without 18-hour Poly-A MP injection. 2E8 particles were injected in each mouse for every particle type.

To confirm that the Poly-A particles comprise sufficient carboxyl groups on the surface with which to conjugate targeting ligands, 1-ethyl-3-[3-(dimethylamino)propyl]carbodiimide hydrochloride (EDC) chemistry was used to conjugate Neutravidin followed by biotinylated anti-ICAM-1 bound to the surface of the particles. 2 µm Poly-A particles were suspended in 50 mM MES buffer and counted using a hemacytometer. $2.2\times10^9$ particles were suspended in 400 µL of 5 mg/mL Neutravidin solution in 50 mM MES. Particles were rotated for 15 minutes, after which 400 µL of 75 mg/mL EDC solution was added, and particles were rotated overnight. Then, 4 mg of glycine was added to the particle solution to quench the reaction, and particles were rotated for 15 minutes. Particles were then centrifuged and resuspended in PBS −/−. After Neutravidin conjugation, $1\times10^7$ particles were incubated in 100 µL of 5 mg/mL biotinylated anti-ICAM-1 in PBS −/− with 2% BSA for 1 hour on rotation. Avidin particles were then stained with Biotin-PE and anti-ICAM particles were stained with goat anti-mouse IgG-fluorescein isothiocyanate (FITC). Particles were then measured on an Attune Flow Cytometer, and compared to R-phycoerythrin (R-PE) and FITC molecules of equivalent soluble fluorochrome (MESF) beads to determine the total number of ligand sites on the particle surface. FIG. 38 shows flow cytometry histogram plots. Poly-A-Avidin and Poly-A-anti-ICAM had 36,819 sites/um$^2$ and 43,235 sites/um$^2$, respectively.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

All publications, published patent documents, and patent applications cited herein are hereby incorporated by reference to the same extent as though each individual publication, published patent document, or patent application was specifically and individually indicated as being incorporated by reference.

We claim:

1. A pharmaceutical composition comprising at least one rod-shaped Poly-A particle wherein Poly-A is salicylate polyanhydride ester that hydrolyzes to salicylic acid, wherein said Poly-A particle is a vascular-targeted Poly-A particle (VTP), wherein a surface of said VTP is bound with an antibody or ligand that targets one or more proteins expressed on a vascular wall and a pharmaceutically acceptable carrier and/or a pharmaceutically acceptable formulation.

2. The pharmaceutical composition of claim 1, wherein said antibody or ligand comprises an anti-E-selectin antibody, an anti-intracellular adhesion molecule-1 antibody (anti-ICAM-1 antibody), an anti-vascular cell adhesion molecule (VCAM)-1 antibody (anti-VCAM-1 antibody), a peptide that binds a selectin or a leukocyte adhesion molecules (LAM), or a carbohydrate that binds a selectin or a LAM.

3. The pharmaceutical composition of claim 1, wherein said rod-shaped Poly-A comprises a smooth surface.

4. The pharmaceutical composition of claim 1, further comprising a diversity of Poly-A particles that differ in dimension, shape, and/or surface morphology.

5. The pharmaceutical composition of claim 1, wherein said rod-shaped Poly-A particle is modified to be a carrier of one or more hydrophobic bioactive compounds or drugs.

6. The pharmaceutical composition of claim 1, wherein said rod-shaped Poly-A particle is modified to be a carrier of one or more hydrophilic bioactive compounds or drugs.

7. The pharmaceutical composition of claim 1, wherein said rod-shaped Poly-A particle is made by the method of:
    a) dissolving polyvinyl alcohol (PVA) with an average molecular weight of 20-70 kDA in water to generate a 1 wt % PVA solution of pH 6-7;
    b) dissolving Poly-A in dichloromethane (DCM);
    c) adding said Poly-A in said DCM to said PVA solution over at least one hour during mixing at >4000 rpm to generate an emulsion;
    d) centrifuging said emulsion;
    e) aspirating a centrifuged solution from a centrifuged pellet;
    f) resuspending said pellet in deionized water to generate suspended Poly-A particles;
    g) washing said suspended Poly-A particles;
    h) lyophilizing said washed Poly-A particles; and
    i) freezing said lyophilized Poly-A particles.

8. The pharmaceutical composition of claim 1, wherein said rod-shaped Poly-A VTP particle is made by the method of:
    a) suspending Poly-A particles in 50 mM MES buffer;
    b) suspending said particles in Neutravidin solution in 50 mM MES;
    c) adding 1-ethyl-3-[3-(dimethylamino) propyl]carbodiimide hydrochloride (EDC) solution to said suspended particles;
    d) adding glycerine to said solution comprising said Poly-A particles;
    e) centrifuging said solution;
    f) resuspending said Poly-A particles in PBS; and
    j) incubating said solution comprising said Poly-A particles with biotinylated anti-ICAM-1 in PBS−/− with 2% BSA.

9. The pharmaceutical composition of claim 1, wherein said rod-shaped Poly-A particle is 2 μm or less in size.

10. A kit comprising a pharmaceutical composition comprising at least one rod-shaped (Poly-A particle) particle wherein Poly-A is salicylate polyanhydride ester that hydrolyzes to salicylic acid, wherein said Poly-A particle is a vascular-targeted Poly-A particle (VTP), wherein a surface of said VTP is bound with an antibody or ligand that targets one or more proteins expressed on a vascular wall and instructions for administering said pharmaceutical composition to a patient diagnosed with vascular thrombosis, inflammatory arthritis, systemic lupus erythematosus (SLE), atherosclerosis, sepsis, acute lung injury arthritis (ALI) and acute respiratory distress syndrome (ARDS).

11. A method of treating or ameliorating a neutrophil-mediated condition in a patient wherein said neutrophil-mediated condition is acute lung injury (ALI) and/or acute respiratory distress syndrome (ARDS), comprising administering to said patient a therapeutically effective amount of a rod-shaped salicylate polyanhydride ester that hydrolyzes to salicylic acid Poly-A particle wherein Poly-A is salicylate polyanhydride ester that hydrolyzes to salicylic acid, wherein said Poly-A particle is a vascular-targeted Poly-A particle (VTP), wherein a surface of said VTP is bound with an antibody or ligand that targets one or more proteins expressed on a vascular wall.

12. The method of claim 11, wherein said patient is a mammal.

13. The method of claim 11, wherein said mammal is a human.

14. The method of claim 11, wherein said administering is intravascular administering.

15. The method of claim 14, wherein said intravascular administering is catheter-directed administration.

16. The method of claim 11, wherein said rod-shaped Poly-A particle comprises a smooth surface.

17. The method of claim 11, further comprising administering a diversity of Poly-A particles that differ in dimension, shape, and/or surface morphology.

18. The method of claim 11, wherein said rod-shaped Poly-A particle is a vascular-targeted Poly-A particle (VTP) wherein a surface of said VTP is bound with an antibody or ligand that targets one or more proteins expressed on a vascular wall and a pharmaceutically acceptable carrier.

19. The method of claim 18, wherein said antibody or ligand comprises an anti-E-selectin antibody, an anti-intracellular adhesion molecule-1 antibody (anti-ICAM-1 antibody), an anti-vascular cell adhesion molecule (VCAM)-1 antibody (anti-VCAM-1 antibody), a peptide that binds a selectin or a leukocyte adhesion molecules (LAM), or a carbohydrate that binds a selectin or a LAM.

\* \* \* \* \*